United States Patent [19]
Mandel et al.

[11] Patent Number: 6,013,769
[45] Date of Patent: Jan. 11, 2000

[54] X-LINKED ADRENOLEUKODYSTROPHY GENE AND CORRESPONDING PROTEIN

[75] Inventors: Jean-Louis Mandel, Schiltigheim; Patrick Aubourg, Sceaux; Jean Mosser; Claude Sarde, both of Strasbourg, all of France

[73] Assignee: Institut National de la Sante et de la Recherche Medicale, Paris Cedex, France

[21] Appl. No.: 08/835,734

[22] Filed: Apr. 10, 1997

Related U.S. Application Data

[62] Division of application No. 08/136,277, Oct. 15, 1993, Pat. No. 5,644,045.

[51] Int. Cl.[7] .................. C07K 14/00; A61K 39/395; C07H 21/04
[52] U.S. Cl. ................. 530/350; 530/300; 530/386; 530/329; 536/23.5
[58] Field of Search .................. 530/350, 300, 530/386, 329; 536/23.5

[56] References Cited

U.S. PATENT DOCUMENTS

| | | | |
|---|---|---|---|
| 5,171,685 | 12/1992 | McElwain et al. | 435/252.33 |
| 5,227,170 | 7/1993 | Sullivan | 424/450 |
| 5,644,045 | 7/1997 | Mandez et al. | 536/23.5 |

OTHER PUBLICATIONS

D. Valle et al., "Penetrating the peroxisome", Nature, vol. 361, Feb. 25, 1993, pp. 682–683.

J. Mosser et al., "Putative X–linked adrenoleukodystrophy gene shares unexpected homology with ABC transporters", Nature, vol. 361, Feb. 25, 1993, pp. 726–730.

R. Feil et al., "Adrenoleukodystrophy: A Complex Chromosomal Rearrangement in the Xq28 Red/Green–Color–Pigment Gene Region Indicates Two Possible Gene Localizations", Am. J. Hum. Genet., vol. 49, 1991, pp. 1361–1371.

P. Aubourg et al., "Frequent Alterations of Visual Pigment Genes in Adrenoleukodystrophy", Am. J. Hum. Genet., vol. 42, 1988, pp. 408–413.

H. Moser et al., "Adrenoleukodystrophy: Phenotypic Variability and Implications for Therapy", J. Inher. Metab. Dis., vol. 15, 1992, 645–664.

A. Barcelo et al., "Identification of a new frameshift mutation (1801delAG) in the ALD gene", Human Molecular Genetics, vol. 3, No. 10, 1994, pp. 1889–1890.

A. Dusty Miller, "Human gene therapy comes of age", Nature, vol. 357, Jun. 11, 1992, pp. 455–460.

R. Parkman, "The Application of Bone Marrow Transplantation to the Treatment of Genetic Diseases", Science, vol. 232, Jun. 13, 1986, pp. 1373–1378.

S. Fuchs et al., "Missense mutations are frequent in the gene for X–chromosomal adrenoleukodystrophy (ALD)", Human Molecular Genetics, vol. 3, No. 10, 1994, pp. 1903–1905.

P. Aubourg et al., "Reversal of Early Neurologic and Neuroradiologic Manifestations of X–Linked Adrenoleukodystrophy by Bone Marrow Transplanation", Reprinted from the New England Journal of Medicine, vol. 322, Jun. 28, 1990, pp. 1860–1866.

P. Fanen et al., "Identification of Mutations in the Putative ATP–binding Domain of the Adrenoleukodystrophy Gene", vol. 94, 1994, pp. 516–520.

C. Sarde et al., "Genomic Organization of the Adrenoleukodystrophy Gene", Genomics, vol. 22, 1994, pp. 13–20.

M. Ligtenberg et al., "Spectrum of Mutations in the Gene Encoding the Adrenoleukodystrophy Protein", Am. J. Hum. Genet., vol. 56(1), 1995 pp. 1–28.

Kamijo, K et al. Nucleotide Sequence of the Human 70KDA Peroximal Membrane Protein. Biochimica et Biophysica Acta vol. 1129, pp. 323–327, Jan. 11, 1992.

George, D.G et al. Current Methods in Sequence Comparison and Analysis. Macromolecular Sequencing and Synthesis Selected Methods and Applications Alan R. Liss, Inc, New York, pp. 127–149, 1988.

Mosser J. et al. Putative X–linked Adrenoleukodystrophy Gene Snares Unexpected Homology with ABC Transporters, Nature, pp. 726–730 vol. 361, Feb. 1993.

Berger, S. L et al. Methods in Enzymology, vol. 152, Academic Press, Inc. pp. 661–673, 1987.

Reeck, G.R et al. "Homology" in Proteins and Nucleic Acids: A Terminology Muddle and a Way Out of It. Cell. vol. 50, p. 667, 1987.

*Primary Examiner*—Elizabeth Kemmerer
*Assistant Examiner*—Nirmal S. Basi
*Attorney, Agent, or Firm*—Young & Thompson

[57] ABSTRACT

The present invention relates to adrenoleukodystrophy proteins and uses thereof. More particularly, the invention relates to human adrenoleukodystrophy proteins. Mutations of the adrenoleukodystrophy protein cause adrenoleukodystrophy or adrenomyelopathy.

3 Claims, 13 Drawing Sheets

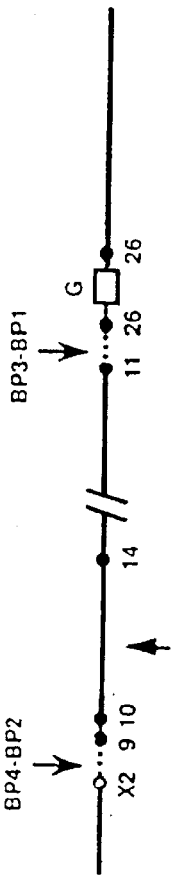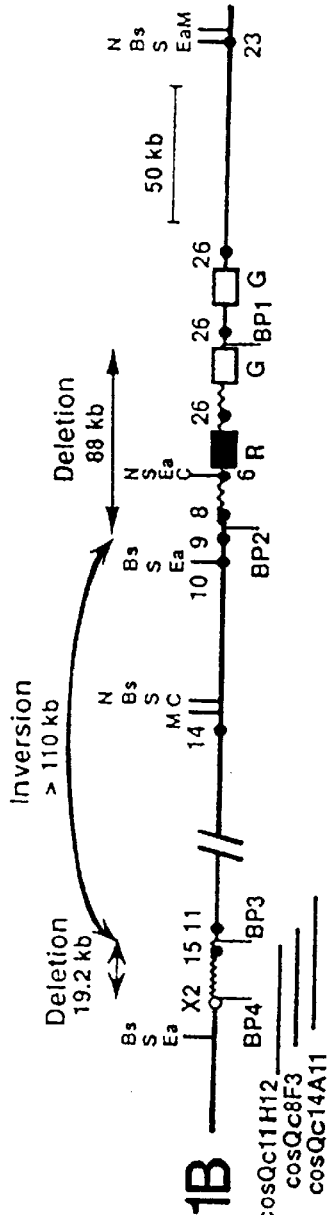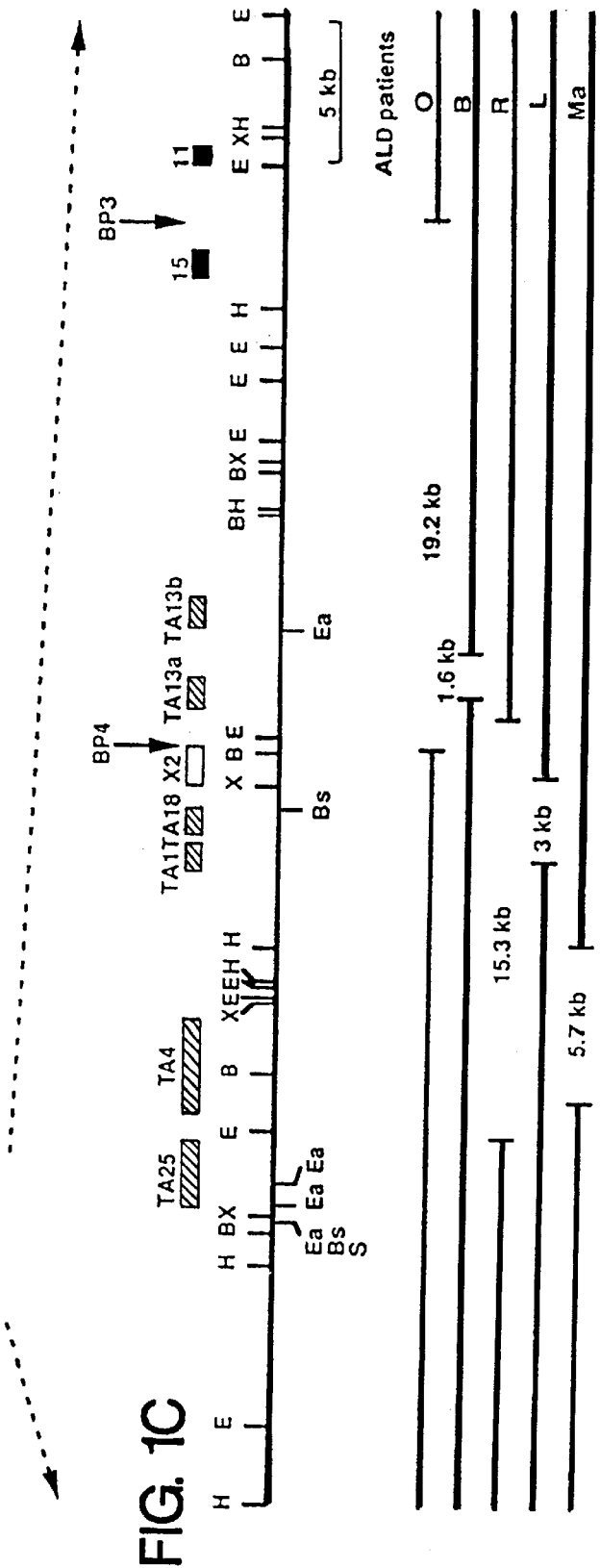
FIG. 1A
FIG. 1B
FIG. 1C

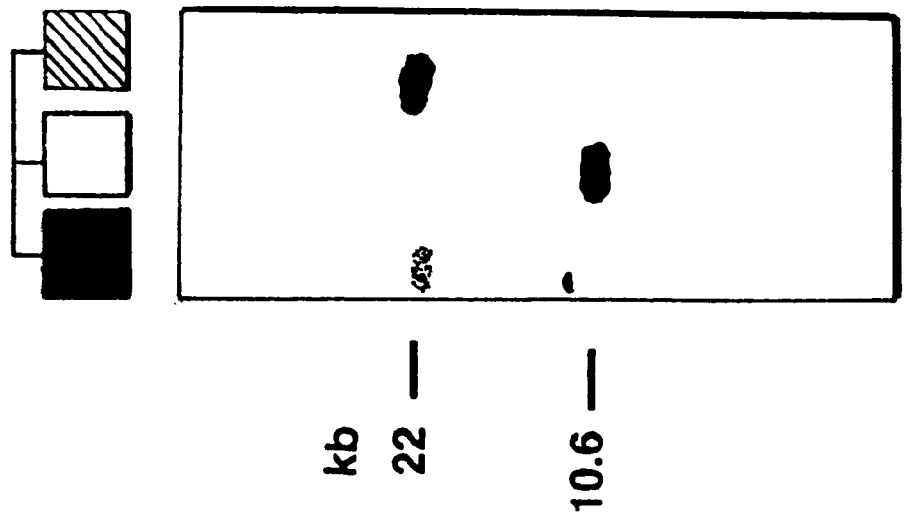
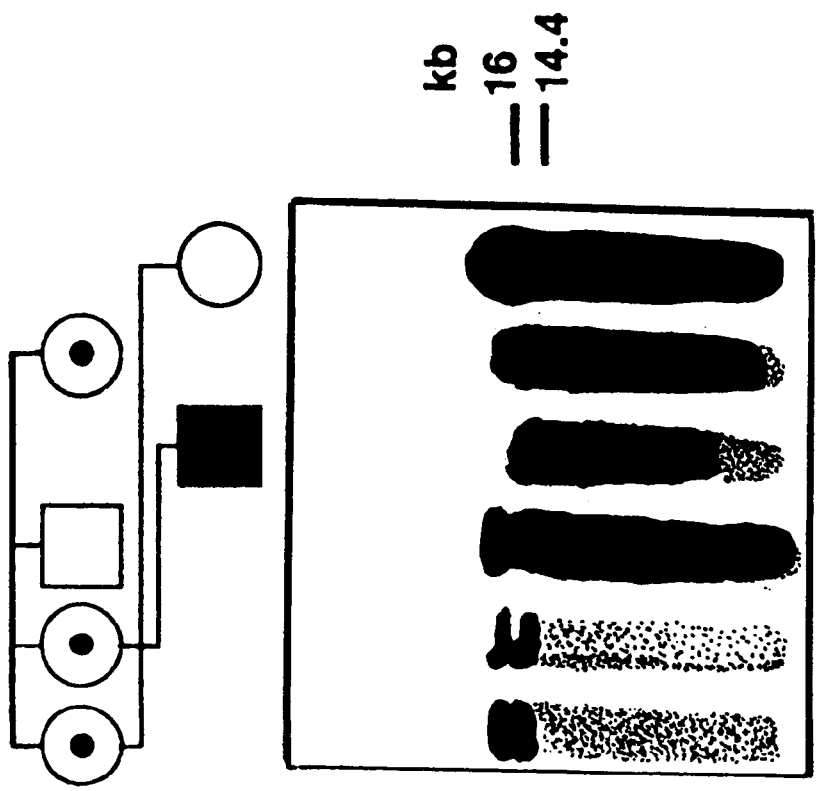

```
PMP70  MAAFSKYLTARNSSLAGAAFLLLCLLHKRRRA--LGL--HGKKSGK--PPLQ--NNEKEG       1- 52
        ::  ::::  :  :::::::  :  ::: :  :  :::   ::
ALDP   MPVLSRPRPWRGNTLKRTAVLLALAAYGAHKVYPLVRQCLAPARGLQAPAGEPTQEASGV      1- 60

PMP70  KKERAVVDKVFFSRLIQILKIMVPRTFCKETGYLVLIAVMLVSRTYCDVWMIQNGTLIES     53-112
        :::   :::::::  ::: :::::::: : :::::
ALDP   AAAKAGMNRVFLQRLLWLLRLLFPRVLCRETGLIALHSAALVSRTFLSVYVARLDGRLAR     61-120

PMP70  GIIGRSRKDFKRYLLNFIAAMPLISLVNNFLKYGLNELKLCFRVRLTKYLYEEYLQAFTY    113-172
        :  :: ::::::::: :::: ::  : :::::: :: ::  :: ::
ALDP   CIARKDPRAFGWQLLQWLLIALPATFVNSAIRYLEGQLALSFRSRLVAHAYRLYFSQQTY    121-180

PMP70  YKKGNLDNRIANPDQLLTQDVEKFCNSVVDLYSNLSKPFLDIVLYIFKLTSAIGAQGPA-    173-231
        :::::::::::: ::::: :  ::    ::: :  :::  ::
ALDP   YRVSNMDGRLRNPDQSLTEDVVAFAASVAHLYSNLTKPLLDVAVTSYTLLRAARSRGAGT    181-240

PMP70  ---SMMAYLVV--SGLFLTRLRRPIGKMTITEQKYEGEYRYVNSRLITNSEEIAFYNGNK    232-286
          :: :::      ::::::::::::::::::::::::::::::
ALDP   AWPSAIAGLVVFLTANVLRAFSPKFGELVAEEARRKGELRYMHSRVVANSEEIAFYGGHE    241-300

PMP70  REKQTVHSVFRKLVEHLHNFILFRFSMGFIDSIIAKYLATVVGYLVVSRPFL-------    287-338
        :   :  ::: ::: :::   :     :: ::   :  :::    :::
ALDP   VELALLQRSYQDLASQINLILLERLWYVMLEQFLMKYVWSASGLLMVAVPIITATGYSES    301-360

PMP70  --DLSHPRHLKSTHSELL---EDYYQSGRMLLR-MSQALGRIVLAGREMTRLAGFTARIT    339-392
          ::   ::  ::::::    :::::  ::: :::::: :  :::  : :::
ALDP   DAEAVKKAALEKKEEELVSERTEAFTIARNLLTAAADAIERIMSSYKEVTELAGYTARVH    361-420
```

FIG. 4B

```
PMP70  ELMQVLKDLNHGKYERTM-VSQQEK------GIEGVQVIPLIPGAGEIIIADNIIKFDHVP        393-446
       : .:: .  .:: :  ::..  :  :::         :  ::::  .: :  . :::: . ::::: .
ALDP   EMFQVFEDVQRCHFKRPRELEDAQAGSGTIGRSGVRVEGPLKIRGQVVDVEQGIICENIP        421-480

PMP70  LATPNGDVLIRDLNFEVRSGANVLICGPNGCGKSSLFRVLGELWPLFGGRLTKPERRKLF        447-506
       :::::::::::::::::::::::::::::::::::::::::::::::::: : :::::
ALDP   IVTPSGEVVVASLNIRVEEGMHLLITGPNGCGKSSLFRILGGLWPTYGGVLYKPPPQRMF        481-540

PMP70  YVPQRPYMTLGTLRDQVIYPDGREDQKRKGISDLVQKEYLDNVQLGHILEREGGWDSVQD        507-566
       :::::::: . ..::::::: :: .. . ::   :. ::: ::: ::::.::::::::
ALDP   YIPQRPYMSVGSLRDQVIYPDSVEDMQRKGYSEQDLEAILDVVHLHHILQREGGWEAMCD        541-600

PMP70  WMDVLSGGEKQRMAMARLFYHKPQFAILDECTSAVSVDVEGYIYSHCRKVGITLFTVSHR        567-626
       : ::::::::::  :::  ::: :  :::::::::: ::::. :: .  ::  ::::::
ALDP   WKDVLSGGEKQRIGMARMFYHRPKYALLDECTSAVSIDVEGKIFQAAKDAGIALLSITHR        601-660

PMP70  KSLWKHHEYYLHMDGRGNYEFKQITEDTVEFGS---------------------------        627-659
       .:::: ::. ::::  : ::::.:: :: :  :
ALDP   PSLWKYHTHLLQFDGEGGWKFEKLDSAARLSLTEEKQRLEQQLAGIPKMQRRLQELCQIL        661-720

PMP70  ------------------------

ALDP   GEAVAPAHVPAPSPQGPGGLQGAST                                     721-745
```

```
                         EXON 1 -        -(1286)- AG
gtggggcaggttgggg tgccgggcacggagggaagcgtgtggcagggagg
cccgggggcaggcagccgtgagcgctggggacagtctggggcgggccggg
gctgatgccaaaggtgtgggcaggccatgggagagccgggctggggtggg
------------------/# 2900 bp/-------------------
cacccaatcgtaacctctggctctcggccttctgatggccaccatggcac
agcgtgtgtgagtggcactgggagaccctgaccatcgcccccacgggagc
tgcccctgtgcatggccaggaagcctctctgtgtctgtcaccccccgcag
GT -(1287)-          - EXON 2 -        -(1467)- AG
gtgagacccagggctccaagaggatccaggccaggtgcctgtcccccata
ccgctgggtgctgagctcacgagggcccaactcagccagcccgccgccca
cttctgctgccggggccaccgaggccctgctgccagccttgatgctttca
------------------/# 6600 bp/-------------------
gcacatagagagaaagagagagagagctggttgccccggcaccatttgca
gaagagcctcgcctttctctccagcggctcattttgactttccgctgtc
tctgccctgcccctccccgcccgccacccacccctctggggctttgcag
AT -(1468)-          - EXON 3 -        -(1610)- AG
gtacccctggcccagccccaccccttgccatccttgccatgcttctctccc
tgcaactggcaggggctgagccagggtcaccctccctcag
GT -(1611)-          - EXON 4 -        -(1729)- AG
gtaaggctgtcccctccctatgagtgaccccgcccctgctgctgctgcag
gtgctgacctgctgccccagctcctcctattcccgctccctcactcaggg
acctccatgtgcttctggcccatcccagtccacccaggacgggagggctg
------------------/# 350 bp/--------------------
ctggaccacaggctgctggtcaggaaccagctggcatgctgccagggatg
ggaatgagggcgtgcagccaggggcacgcagactccccagaatgcagagg
ggtcgccaccactccctctccaccccagccccgctgtgctgtcttctgcag
GC -(1730)-          - EXON 5 -        -(1840)- GG
gtaggtccagcggggagggcgccagccacgcacatatgcaagcctcagcc
cttggcttcccgcctgtctgtgctggcaacagccattgtccctagatgta
cgtggcaggtgggccaaggtcaaggtgagagaccaacgtgtctctgactg
------------------/# 3000 bp/-------------------
tccccaggccctgctgtcccttatcaagagatcaagaatggcctgcgtg
ctggcctcgggcattgggagcctctcaaggctggtcaggaggccataggg
tacgggaaggggcctgcgctctctggcgtcagcggctgttgccctgcag
GT -(1841)-          - EXON 6 -        -(1986)- AG
gtaaggaagcccgtgcgcctctcctccacctcttcctgcctgtgcgctca
cacatggcttcctgcagaggccaggaagtggtgaagagtcagcacctca
ggagaggacactgaggcactgtccccagagccagagacgggctgtggttc
ctgctccctccaaaccgcccgatccactgccctgttttggatctgtgtg
gggtgtgtgcacgggcggcgatgtgagcgtgtggatgcgtgtgagcgtgg
catgtggacactgcctgggaggcgcagagtatcttgggggaggcagagcc
ggcccttccctccgtggacacccagctttcccacag
GC -1987)-           - EXON 7 -        -(2132)- AG
gtaggaggcctggggctggcagccacccttgtcccaccctggcctctcc
cttggcctccagggagtgaagattacctcaacatccagagtctaaagtgc
caggtgccacggggcggggcagaggctgctaccagggaggaccaacacca
------------------/# 1700 bp/-------------------
atgattaatgcctgtcagacagacaaggacgcagaggcacaggggccctg
tcgtcacagctagctcattcccgcagctcccccagctccccggctggccc
ccgggtctgggtgctggtggaactgagccaagaccattgcccccgcctag
GT -(2133)-          - EXON 8 -        -(2218)- AG
gtgagcactccggaccggcaggctccctggggtcccctggaaggggaagt
agcagctgtggggaggcctgggctcagtggagcctgagccgggctggggt
gttgggccctggagggtgcacagactctcctctcggcccggaccccag
GC -(2219)-          - EXON 9 -        -(2344)- TG
gtaggtgccctgtctccctgcctggggtcggtgggagtgcctgcctgagg
ggaggaggtggcctggcggccccggcagcagcaggcggctgtcatcagca
gcccccgtgccgtgccctgaccctgtccctctcctggccag
GA -(2345)-          - EXON 10
```

FIG. 6

GCGGAGCGGACGCGCCTGTGCCCCGGGAGGGGCGCCACCGGGGAGGAGGAGGA
GGAGAAGGTGGAGAGAAGACGCCCCCTCTGCCCGAGACCTCTCAAGGCCCTGACCTC
AGGGGCCAGGGCACTGACAGGACAGGAGAGCCAAGTTCCTCCACTTGGGCTGCCCGAAGA
GGCCGGACCCCTGGAGGGCCCTGAGCGCCACCAGGGCCCCAGCAGGGCACCACCCCGGGG
GCCTAAAGCGACAGTCTCAGGGCCATCGCAAGGTTTCCAGTTGCCTAGACAACAGGCCC
AGGGTCAGAGCAACAATCCTTCCAGCCACCTGCCTCAACTGCTGCCCCAGGCACCAGCCC
CAGTCCCTACGCGGCCAGCCAGCCCAGTGACATGCCGGTGCTCTCCAGGCCCCGGCCCTG
GCGGGGAACACGCTGAAGCGCACCGGCCGTGCCTGCCCTGCGCCCTCTGCGCGCCCAGCCCA
CAAAGTCTACCCCTTGGTGCGCCAGTGCCCAGTGCCCGGGTCTTCAGGCGCCCCGC
CGGGGAGCCCACGCAGGAGGCCTCTGGCTTCCCCGGGGTCGGCCATGAACCGGGT
ATTCCTGCAGCGGCTGCCTCCTGTGCTCGGCGCCTTGGCTGAGCCGCACCTTCCTGTCGGGGA
GACGGGCTGCTGCCCTGGACGGAAGGCTGGCCGCTGGTGAGCCGCCCGCAAGGACCCGCGGCTTT
TGTGCCCGCCTGGACGGAAGGCTGGCCGCTGGTGAGCCGCCCGCAAGGACCCGCGGCTTT
TGGCTGGCAGTGCTGCAGTGCCCCAACTGGCCCGTCGTTCCGCAGCCGTCTCTGGTGGCCCACGC
CATCCGTTACCTGGAGGCCAACTGGCCCGTCGTTCCGCAGCCGTCTCTGGTGGCCCACGC
CTACCGCCTCTACTTCTCCCAGCAGATCTCTGACGGAGGACGTGGTGGCCTTTGCGCCTCTGTGGCT
TCGCAACCCTGACCAGTCTCTGACGGAGGACGTGGTGGCCTTCTGTGACTTCCTACACCCTGCT
CCTCTACTCCAACCTGACCAAGCCACACTCCTGACGTGCTGTGACTTCCTACACCCTGCT
TCGGGCGGCCCGCTCCCGTGAGCCGGCCTTCTCGCCCATCGCCGGCCTCGT
GGTGTTCCTCACGCCAACGTGCTGCGGGGAGCTGCGCTACAGTTCGGGAGCTGGTGGC
AGAGGAGGCCGCGGAAGGCGCGGAGCTGCGCTACATGCACTCGCGTGTGGTGGCCAACTC
GGAGGAGATCGCTTCTATGGGGGCCATGAGgtggggcaggaggcccgggggaggcccgggggcgga
gggaagcgtgtggcaggaggcccgggggcaggcagccgtgagcggtggggacagtctgg
ggcgggccggggctgatgccaaaggtgtgggcaggccatgggcagccggagagccggggctggggtgg
g

FIG. 7A

```
cacccaatcgtaacctctggctctctgcctctcggcttctgatggccaccatggcacagcgtgtgtg
agtggcactgggagaccctgaccatcgccccacgggagctgcccctgtgcatggccagg
aagcctctctgtgtctgtcacccccgcagGTGGAGCTGGCCCTGCTACAGCGCTCCTAC
CAGGACCTGGCCTGCCAGATCAACCTCATCCTTCTGAACGCCTGTGGTATGTTATGCTG
GAGCAGTTCCTCATGAAGTATGTGTGGAGCGCCTCGGGCCTGCTCATGGTGGCTGTCCCC
ATCATCACTGCCACTGGCTACTCAGAGTCAGgtgagacccaggctccaagaggatccag
gccaggggcctgtccccataccgctgggtgctgagctcacgagggcccaactcagccag
cccgccgccacttctgctgccggggccaccgaggccctgctgccagccttgatgctttc
a gcacatagagagagaaagagagagagagagagctggttgccccgcaccattgcagaagagcctc
gcctttctccagcggctcattttgactttccgctgtctctgccctgccccctccccgc
cccgccaccacccctctggggctttgcagATGCAGAGGCCGTGAAGAGGCAGCCTTGG
AAAGAGGAGGAGGAGAGCTGGTGTGAGCGAGCGCACAGAAGCCTTCACTATTGCCCGCAACC
TCCTGACAGCGGCTGCAGATGCCATTGAGCGGATCATGTCGTCGTACAAGGAGtaccccc
tggcccagccagtcccccacccttgccatccttgccatgcttctctccctgcaactggcagggct
gagccaggtcaccctcccctcagGTGACGGAGCTGGCTGCTCACTTCAAGAGGCCCAG
AGATGTTCCAGGTATTTGAAGATGTTCAGCGCTGTGGACCATAGGCCGGTCTCGGTCTCGTGTC
AGGACGCTCAGGCGGGTCTCGGACCATAGCCGGGTCTCCCCTATGAGTGACCCGCCCCCTGCTGC
TGAAGATCCGAGtaaggctgtccccctgctccccagctcctcctattcccgctccctcactcagggacctccat
agtgctgacctgctgccccagctcctcctattcccgctccctcactcagggacctccat
gtgcttctgcccatcccagtcccaccaggacgggagggctg ctggaccacaggctgctggtcaggaaccagctggcatgctgccaggatgggaatgaggg
cgtgcagcaggggcacgcagactcccagaatgcagaggggtcgccaccactccctc
caccccagccccgctgtgctgctgtctctgcagGCCAGTGTGGATGTGGAACAGGGATCA
```

FIG. 7B

TCTGCGAGAACATCCCCATCGTCACGCCCTCAGGAGAGGTGGTGGCCAGCCTCAACA
TCAGGgtaggtccagcgggaggcgccagccacgcacatatgcaagcctcagccctgg
cttcccgcctgtctgctggcaacagccattgtccctagatgtacgtggcaggtgggcc
aaggtcaaggtgagagaccaacgtgtctctgactg tcccccagcccctgctgtccctatcaagagatcaagaatgcctgcgtgctgccctcgg
gcattgggagcctctcaaggctggtcaggaggccataggtacgggaagggcctgcgct
ctctggtcgtcagcggctgttgccctgcagtGTGGAGGAAGGCATGCATCTGCTCATCACA
GGCCCCAATGCTGCGGCAAGAGCTCCCTGTTCCGGATCCTGGGCTCTGGCCCACG
TACGGTGGTGTGCTCTACAAGCCCCACCCAGCGCATGTTCTACATCCCGCAGAGgtaa
ggaagcccgtgcgcgcctctcctccacctcttcctgcctgtgcgctcacacatggcttcctg
cagaggccaggaagtggtgaagagtcagcacctcaggagagacactgaggcactgtcc
ccagagccagagacgggctggtgtggtcctgctccctccaaacccgcccgatccactgccct
gttttggatctgtgtggggtgtgtgtgcacgggcgatgtgagcgtgtggatgcgtgtga
gcgtggcatgtggacactgcctggaggcgcagagtatcttgggggaggcaggagccggcc
cttccctccgtggacacccagctttcccacagGCCCTACAGTTCTGTGGCCTCCCTGCGT
GACCAGGTGATCTACCCGGACTCAGTGACGTCGTGACACTGCAAAGGAAGGCTACTCGGAGCAG
GACCTGGAAGCCATCCTGGACGTCGTGACAGCCACCAGACCCTGCAGCGGGAGGGAGgt
aggaggcctgggcgtggcctggcagcacccctttgtcccacccttgcctctcctttggcctccag
ggagtgaagattacctcaacatccagagtctaaagtgccaggtgccacgggggcgggcag
aggctgctaccaggggaggaccaacacca

FIG. 7C

```
atgattaatgcctgtcagacagacaaggacgcagaggcacagggccctgtcgtcacagc
tagctcattcccgcagctccccgctccccgcctggcctctgggtgctggtgg
aactgagccaagaccattgccccgcctagGTTGGGAGGCTATGTGTGACTGGAAGGACG
TCCTGTGGGTGGCGAGAAGCAGAGAATCGGCATGCCCGCATGTTCTACCACAGgtgag
cactccggaccggcaggctcccctgggtccctggaaggggaagtagcagctgtggggag
GCCTGGGCTCAGTGGGCCTGAGCCTGTGTTGGGCTGTGTTGGCCTGGAGGGTGCACAGAC
TCTCCTCTCGGCCCCAGCCCAAGTACGCCCCTGGATGAATGCACCAGCGC
CGTGAGCATGACGTGGAAGGCAAGATCTTCCAGGCGGGGCATTGCCCT
GCTCCATCACCGGCCCTCCCTGTGtaggtgccctgtcctccctgggtcg
gtgggagtgcctgcctgaggggaggtggcctggccctgggccccgagcagcaggcggct
gtcatcagcagccccgtgccgtgccctgacccctgtccctctcctgccagGAAATACC
ACACACACTTGCTACAGTTCGATGGGAGGGCGGCTGGAAGTTCGAGAAGCTGGACTCAG
CTGCCCGCCTGAGCCTTGACGGAGGAGAAGCAGCTGGGCAGCAGCTGGCGGGCATTC
CCAAGATGCAGCGGCCTCCAGAGCTCTGCCCCTGGTCGCCTCCAGGCTGCCTCCACCTGAC
CGCATGTGCCGGCACCTAGCCCGCCACCTGCCCCGCCCCCCAAGCTCGATCACATGAAGGAGACAGCAGC
ACAACCGTCCCCGCCCTGCCCCGCCCCCCGCCCCTGCATGCCTGCCCTCCACCTACAAGGAGACAGCAGC
ACCCACCATGCACGCCACCGCCACCTGCCCCTGGCCCCTCCTGCCCCTCCTAGAAAACCCTTC
CCGCC
```

FIG. 7D

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 2750 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 387..2624

(xi) SEQUENCE DESCRIPTION: SEQ ID NO:1:

```
GCGGACGGAC GCGCCTGGTG CCCCGGGGAG GGGCGCCACC GGGGGAGGAG GAGGAGGAGA      60

AGGTGGAGAG GAAGAGACGC CCCCTCTGCC CGAGACCTCT CAAGGCCCTG ACCTCAGGGG     120

CCAGGGCACT GACAGGACAG GAGAGCCAAG TTCCTCCACT TGGGCTGCCC GAAGAGGCCG     180

CGACCCTGGA GGGCCCTGAG CCCACCGCAC CAGGGGCCCC AGCACCACCC CGGGGGCCTA     240

AAGCGACAGT CTCAGGGGCC ATCGCAAGGT TTCCAGTTGC CTAGACAACA GGCCCAGGGT     300

CAGAGCAACA ATCCTTCCAG CCACCTGCCT CAACTGCTGC CCCAGGCACC AGCCCCAGTC     360

CCTACGCGGC AGCCAGCCCA GGTGAC ATG CCG GTG CTC TCC AGG CCC CGG CCC     413
                              Met Pro Val Leu Ser Arg Pro Arg Pro
                                1               5

TGG CGG GGG AAC ACG CTG AAG CGC ACG GCC GTG CTC CTG GCC CTC GCG     461
Trp Arg Gly Asn Thr Leu Lys Arg Thr Ala Val Leu Leu Ala Leu Ala
 10              15                  20                  25

GCC TAT GGA GCC CAC AAA GTC TAC CCC TTG GTG CGC CAG TGC CTG GCC     509
Ala Tyr Gly Ala His Lys Val Tyr Pro Leu Val Arg Gln Cys Leu Ala
                30                  35                  40

CCG GCC AGG GGT CTT CAG GCG CCC GCC GGG GAG CCC ACG CAG GAG GCC     557
Pro Ala Arg Gly Leu Gln Ala Pro Ala Gly Glu Pro Thr Gln Glu Ala
            45                  50                  55

TCC GGG GTC GCG GCG GCC AAA GCT GGC ATG AAC CGG GTA TTC CTG CAG     605
Ser Gly Val Ala Ala Ala Lys Ala Gly Met Asn Arg Val Phe Leu Gln
        60                  65                  70

CGG CTC CTG TGG CTC CTG CGG CTG CTG TTC CCC CGG GTC CTG TGC CGG     653
Arg Leu Leu Trp Leu Leu Arg Leu Leu Phe Pro Arg Val Leu Cys Arg
    75                  80                  85

GAG ACG GGG CTG CTG GCC CTG CAC TCG GCC GCC TTG GTG AGC CGC ACC     701
Glu Thr Gly Leu Leu Ala Leu His Ser Ala Ala Leu Val Ser Arg Thr
 90                  95                 100                 105

TTC CTG TCG GTG TAT GTG GCC CGC CTG GAC GGA AGG CTG GCC CGC TGC     749
Phe Leu Ser Val Tyr Val Ala Arg Leu Asp Gly Arg Leu Ala Arg Cys
                110                 115                 120
```

-continued

| | | |
|---|---|---|
| ATC GCC CGC AAG GAC CCG CGG GCT TTT GGC TGG CAG CTG CTG CAG TGG<br>Ile Ala Arg Lys Asp Pro Arg Ala Phe Gly Trp Gln Leu Leu Gln Trp<br>            125                   130                  135 | 797 |

CTC CTC ATC GCC CTC CCT GCT ACC TTC GTC AAC AGT GCC ATC CGT TAC    845
Leu Leu Ile Ala Leu Pro Ala Thr Phe Val Asn Ser Ala Ile Arg Tyr
        140                145                150

CTG GAG GGC CAA CTG GCC CTG TCG TTC CGC AGC CGT CTG GTG GCC CAC    893
Leu Glu Gly Gln Leu Ala Leu Ser Phe Arg Ser Arg Leu Val Ala His
     155                   160                165

GCC TAC CGC CTC TAC TTC TCC CAG CAG ACC TAC TAC CGG GTC AGC AAC    941
Ala Tyr Arg Leu Tyr Phe Ser Gln Gln Thr Tyr Tyr Arg Val Ser Asn
170                   175                180                185

ATG GAC GGG CGG CTT CGC AAC CCT GAC CAG TCT CTG ACG GAG GAC GTG    989
Met Asp Gly Arg Leu Arg Asn Pro Asp Gln Ser Leu Thr Glu Asp Val
               190                 195                200

GTG GCC TTT GCG GCC TCT GTG GCC CAC CTC TAC TCC AAC CTG ACC AAG  1037
Val Ala Phe Ala Ala Ser Val Ala His Leu Tyr Ser Asn Leu Thr Lys
             205                 210              215

CCA CTC CTG GAC GTG GCT GTG ACT TCC TAC ACC CTG CTT CGG GCG GCC  1085
Pro Leu Leu Asp Val Ala Val Thr Ser Tyr Thr Leu Leu Arg Ala Ala
220                   225                230

CGC TCC CGT GGA GCC GGC ACA GCC TGG CCC TCG GCC ATC GCC GGC CTC  1133
Arg Ser Arg Gly Ala Gly Thr Ala Trp Pro Ser Ala Ile Ala Gly Leu
     235                   240                245

GTG GTG TTC CTC ACG GCC AAC GTG CTG CGG GCC TTC TCG CCC AAG TTC  1181
Val Val Phe Leu Thr Ala Asn Val Leu Arg Ala Phe Ser Pro Lys Phe
250                   255                260              265

GGG GAG CTG GTG GCA GAG GAG GCG CGG CGG AAG GGG GAG CTG CGC TAC  1229
Gly Glu Leu Val Ala Glu Glu Ala Arg Arg Lys Gly Glu Leu Arg Tyr
             270                 275                280

ATG CAC TCG CGT GTG GTG GCC AAC TCG GAG GAG ATC GCC TTC TAT GGG  1277
Met His Ser Arg Val Val Ala Asn Ser Glu Glu Ile Ala Phe Tyr Gly
             285                 290              295

GGC CAT GAG GTG GAG CTG GCC CTG CTA CAG CGC TCC TAC CAG GAC CTG  1325
Gly His Glu Val Glu Leu Ala Leu Leu Gln Arg Ser Tyr Gln Asp Leu
        300                  305               310

GCC TCG CAG ATC AAC CTC ATC CTT CTG GAA CGC CTG TGG TAT GTT ATG  1373
Ala Ser Gln Ile Asn Leu Ile Leu Leu Glu Arg Leu Trp Tyr Val Met
    315                  320                325

CTG GAG CAG TTC CTC ATG AAG TAT GTG TGG AGC GCC TCG GGC CTG CTC  1421
Leu Glu Gln Phe Leu Met Lys Tyr Val Trp Ser Ala Ser Gly Leu Leu
330                   335                340              345

ATG GTG GCT GTC CCC ATC ATC ACT GCC ACT GGC TAC TCA GAG TCA GAT  1469
Met Val Ala Val Pro Ile Ile Thr Ala Thr Gly Tyr Ser Glu Ser Asp
             350                 355              360

GCA GAG GCC GTG AAG AAG GCA GCC TTG GAA AAG AAG GAG GAG GAG CTG  1517
Ala Glu Ala Val Lys Lys Ala Ala Leu Glu Lys Lys Glu Glu Glu Leu
             365                 370              375

GTG AGC GAG CGC ACA GAA GCC TTC ACT ATT GCC CGC AAC CTC CTG ACA  1565
Val Ser Glu Arg Thr Glu Ala Phe Thr Ile Ala Arg Asn Leu Leu Thr
        380                  385               390

GCG GCT GCA GAT GCC ATT GAG CGG ATC ATG TCG TCG TAC AAG GAG GTG  1613
Ala Ala Ala Asp Ala Ile Glu Arg Ile Met Ser Ser Tyr Lys Glu Val
395                   400                405

ACG GAG CTG GCT GGC TAC ACA GCC CGG GTG CAC GAG ATG TTC CAG GTA  1661
Thr Glu Leu Ala Gly Tyr Thr Ala Arg Val His Glu Met Phe Gln Val
410                   415                420              425

TTT GAA GAT GTT CAG CGC TGT CAC TTC AAG AGG CCC AGG GAG CTA GAG  1709
Phe Glu Asp Val Gln Arg Cys His Phe Lys Arg Pro Arg Glu Leu Glu
             430                 435              440

```
GAC GCT CAG GCG GGG TCT GGG ACC ATA GGC CGG TCT GGT GTC CGT GTG    1757
Asp Ala Gln Ala Gly Ser Gly Thr Ile Gly Arg Ser Gly Val Arg Val
        445                 450                 455

GAG GGC CCC CTG AAG ATC CGA GGC CAG GTG GTG GAT GTG GAA CAG GGG    1805
Glu Gly Pro Leu Lys Ile Arg Gly Gln Val Val Asp Val Glu Gln Gly
            460                 465                 470

ATC ATC TGC GAG AAC ATC CCC ATC GTC ACG CCC TCA GGA GAG GTG GTG    1853
Ile Ile Cys Glu Asn Ile Pro Ile Val Thr Pro Ser Gly Glu Val Val
    475                 480                 485

GTG GCC AGC CTC AAC ATC AGG GTG GAG GAA GGC ATG CAT CTG CTC ATC    1901
Val Ala Ser Leu Asn Ile Arg Val Glu Glu Gly Met His Leu Leu Ile
490                 495                 500                 505

ACA GGC CCC AAT GGC TGC GGC AAG AGC TCC CTG TTC CGG ATC CTG GGT    1949
Thr Gly Pro Asn Gly Cys Gly Lys Ser Ser Leu Phe Arg Ile Leu Gly
                510                 515                 520

GGG CTC TGG CCC ACG TAC GGT GGT GTG CTC TAC AAG CCC CCA CCC CAG    1997
Gly Leu Trp Pro Thr Tyr Gly Gly Val Leu Tyr Lys Pro Pro Pro Gln
            525                 530                 535

CGC ATG TTC TAC ATC CCG CAG AGG CCC TAC ATG TCT GTG GGC TCC CTG    2045
Arg Met Phe Tyr Ile Pro Gln Arg Pro Tyr Met Ser Val Gly Ser Leu
        540                 545                 550

CGT GAC CAG GTG ATC TAC CCG GAC TCA GTG GAG GAC ATG CAA AGG AAG    2093
Arg Asp Gln Val Ile Tyr Pro Asp Ser Val Glu Asp Met Gln Arg Lys
555                 560                 565

GGC TAC TCG GAG CAG GAC CTG GAA GCC ATC CTG GAC GTC GTG CAC CTG    2141
Gly Tyr Ser Glu Gln Asp Leu Glu Ala Ile Leu Asp Val Val His Leu
570                 575                 580                 585

CAC CAC ATC CTG CAG CGG GAG GGA GGT TGG GAG GCT ATG TGT GAC TGG    2189
His His Ile Leu Gln Arg Glu Gly Gly Trp Glu Ala Met Cys Asp Trp
                590                 595                 600

AAG GAC GTC CTG TCG GGT GGC GAG AAG CAG AGA ATC GGC ATG GCC CGC    2237
Lys Asp Val Leu Ser Gly Gly Glu Lys Gln Arg Ile Gly Met Ala Arg
            605                 610                 615

ATG TTC TAC CAC AGG CCC AAG TAC GCC CTC CTG GAT GAA TGC ACC AGC    2285
Met Phe Tyr His Arg Pro Lys Tyr Ala Leu Leu Asp Glu Cys Thr Ser
        620                 625                 630

GCC GTG AGC ATC GAC GTG GAA GGC AAG ATC TTC CAG GCG GCC AAG GAC    2333
Ala Val Ser Ile Asp Val Glu Gly Lys Ile Phe Gln Ala Ala Lys Asp
    635                 640                 645

GCG GGC ATT GCC CTG CTC TCC ATC ACC CAC CGG CCC TCC CTG TGG AAA    2381
Ala Gly Ile Ala Leu Leu Ser Ile Thr His Arg Pro Ser Leu Trp Lys
650                 655                 660                 665

TAC CAC ACA CAC TTG CTA CAG TTC GAT GGG GAG GGC GGC TGG AAG TTC    2429
Tyr His Thr His Leu Leu Gln Phe Asp Gly Glu Gly Gly Trp Lys Phe
                670                 675                 680

GAG AAG CTG GAC TCA GCT GCC CGC CTG AGC CTG ACG GAG GAG AAG CAG    2477
Glu Lys Leu Asp Ser Ala Ala Arg Leu Ser Leu Thr Glu Glu Lys Gln
            685                 690                 695

CGG CTG GAG CAG CAG CTG GCG GGC ATT CCC AAG ATG CAG CGG CGC CTC    2525
Arg Leu Glu Gln Gln Leu Ala Gly Ile Pro Lys Met Gln Arg Arg Leu
        700                 705                 710

CAG GAG CTC TGC CAG ATC CTG GGC GAG GCC GTG GCC CCA GCG CAT GTG    2573
Gln Glu Leu Cys Gln Ile Leu Gly Glu Ala Val Ala Pro Ala His Val
    715                 720                 725

CCG GCA CCT AGC CCG CAA GGC CCT GGT GGC CTC CAG GGT GCC TCC ACC    2621
Pro Ala Pro Ser Pro Gln Gly Pro Gly Gly Leu Gln Gly Ala Ser Thr
730                 735                 740                 745

TGACACAACC GTCCCCGGCC CCTGCCCCGC CCCCAAGCTC GGATCACATG AAGGAGACAG    2681

CAGCACCCAC CCATGCACGC ACCCCGCCCC TGCATGCCTG GCCCCTCCTC CTAGAAAACC    2741
```

CTTCCCGCC                                                                2750

(2) INFORMATION FOR SEQ ID NO:2:

(i) SEQUENCE CHARACTERISTICS:
        (A) LENGTH: 745 amino acids
        (B) TYPE: amino acid
        (D) TOPOLOGY: linear (ii) MOLECULE TYPE: protein (xi) SEQUENCE DESCRIPTION: SEQ ID NO:2:

```
Met Pro Val Leu Ser Arg Pro Arg Pro Trp Arg Gly Asn Thr Leu Lys
 1               5                  10                  15

Arg Thr Ala Val Leu Leu Ala Leu Ala Ala Tyr Gly Ala His Lys Val
            20                  25                  30

Tyr Pro Leu Val Arg Gln Cys Leu Ala Pro Ala Arg Gly Leu Gln Ala
        35                  40                  45

Pro Ala Gly Glu Pro Thr Gln Glu Ala Ser Gly Val Ala Ala Ala Lys
    50                  55                  60

Ala Gly Met Asn Arg Val Phe Leu Gln Arg Leu Leu Trp Leu Leu Arg
65                  70                  75                  80

Leu Leu Phe Pro Arg Val Leu Cys Arg Glu Thr Gly Leu Leu Ala Leu
                85                  90                  95

His Ser Ala Ala Leu Val Ser Arg Thr Phe Leu Ser Val Tyr Val Ala
            100                 105                 110

Arg Leu Asp Gly Arg Leu Ala Arg Cys Ile Ala Arg Lys Asp Pro Arg
        115                 120                 125

Ala Phe Gly Trp Gln Leu Leu Gln Trp Leu Leu Ile Ala Leu Pro Ala
    130                 135                 140

Thr Phe Val Asn Ser Ala Ile Arg Tyr Leu Glu Gly Gln Leu Ala Leu
145                 150                 155                 160

Ser Phe Arg Ser Arg Leu Val Ala His Ala Tyr Arg Leu Tyr Phe Ser
                165                 170                 175

Gln Gln Thr Tyr Tyr Arg Val Ser Asn Met Asp Gly Arg Leu Arg Asn
            180                 185                 190

Pro Asp Gln Ser Leu Thr Glu Asp Val Val Ala Phe Ala Ala Ser Val
        195                 200                 205

Ala His Leu Tyr Ser Asn Leu Thr Lys Pro Leu Leu Asp Val Ala Val
    210                 215                 220

Thr Ser Tyr Thr Leu Leu Arg Ala Ala Arg Ser Arg Gly Ala Gly Thr
225                 230                 235                 240

Ala Trp Pro Ser Ala Ile Ala Gly Leu Val Val Phe Leu Thr Ala Asn
                245                 250                 255

Val Leu Arg Ala Phe Ser Pro Lys Phe Gly Glu Leu Val Ala Glu Glu
            260                 265                 270

Ala Arg Arg Lys Gly Glu Leu Arg Tyr Met His Ser Arg Val Val Ala
        275                 280                 285

Asn Ser Glu Glu Ile Ala Phe Tyr Gly Gly His Glu Val Glu Leu Ala
    290                 295                 300

Leu Leu Gln Arg Ser Tyr Gln Asp Leu Ala Ser Gln Ile Asn Leu Ile
305                 310                 315                 320

Leu Leu Glu Arg Leu Trp Tyr Val Met Leu Glu Gln Phe Leu Met Lys
                325                 330                 335

Tyr Val Trp Ser Ala Ser Gly Leu Leu Met Val Ala Val Pro Ile Ile
            340                 345                 350
```

Thr Ala Thr Gly Tyr Ser Glu Ser Asp Ala Glu Ala Val Lys Lys Ala
            355                 360                 365

Ala Leu Glu Lys Lys Glu Glu Leu Val Ser Glu Arg Thr Glu Ala
370                 375                 380

Phe Thr Ile Ala Arg Asn Leu Leu Thr Ala Ala Asp Ala Ile Glu
385                 390                 395                 400

Arg Ile Met Ser Ser Tyr Lys Glu Val Thr Glu Leu Ala Gly Tyr Thr
                405                 410                 415

Ala Arg Val His Glu Met Phe Gln Val Phe Glu Asp Val Gln Arg Cys
            420                 425                 430

His Phe Lys Arg Pro Arg Glu Leu Glu Asp Ala Gln Ala Gly Ser Gly
            435                 440                 445

Thr Ile Gly Arg Ser Gly Val Arg Val Glu Gly Pro Leu Lys Ile Arg
450                 455                 460

Gly Gln Val Val Asp Val Glu Gln Gly Ile Ile Cys Glu Asn Ile Pro
465                 470                 475                 480

Ile Val Thr Pro Ser Gly Glu Val Val Ala Ser Leu Asn Ile Arg
            485                 490                 495

Val Glu Glu Gly Met His Leu Leu Ile Thr Gly Pro Asn Gly Cys Gly
            500                 505                 510

Lys Ser Ser Leu Phe Arg Ile Leu Gly Gly Leu Trp Pro Thr Tyr Gly
            515                 520                 525

Gly Val Leu Tyr Lys Pro Pro Pro Gln Arg Met Phe Tyr Ile Pro Gln
530                 535                 540

Arg Pro Tyr Met Ser Val Gly Ser Leu Arg Asp Gln Val Ile Tyr Pro
545                 550                 555                 560

Asp Ser Val Glu Asp Met Gln Arg Lys Gly Tyr Ser Glu Gln Asp Leu
            565                 570                 575

Glu Ala Ile Leu Asp Val Val His Leu His His Ile Leu Gln Arg Glu
            580                 585                 590

Gly Gly Trp Glu Ala Met Cys Asp Trp Lys Asp Val Leu Ser Gly Gly
            595                 600                 605

Glu Lys Gln Arg Ile Gly Met Ala Arg Met Phe Tyr His Arg Pro Lys
            610                 615                 620

Tyr Ala Leu Leu Asp Glu Cys Thr Ser Ala Val Ser Ile Asp Val Glu
625                 630                 635                 640

Gly Lys Ile Phe Gln Ala Ala Lys Asp Ala Gly Ile Ala Leu Leu Ser
                645                 650                 655

Ile Thr His Arg Pro Ser Leu Trp Lys Tyr His Thr His Leu Leu Gln
            660                 665                 670

Phe Asp Gly Glu Gly Gly Trp Lys Phe Glu Lys Leu Asp Ser Ala Ala
            675                 680                 685

Arg Leu Ser Leu Thr Glu Glu Lys Gln Arg Leu Glu Gln Gln Leu Ala
690                 695                 700

Gly Ile Pro Lys Met Gln Arg Arg Leu Gln Glu Leu Cys Gln Ile Leu
705                 710                 715                 720

Gly Glu Ala Val Ala Pro Ala His Val Pro Ala Pro Ser Pro Gln Gly
            725                 730                 735

Pro Gly Gly Leu Gln Gly Ala Ser Thr
            740                 745

(2) INFORMATION FOR SEQ ID NO:3:

(i) SEQUENCE CHARACTERISTICS:
      (A) LENGTH: 659 amino acids (B) TYPE: amino acid
(D) TOPOLOGY: linear (ii) MOLECULE TYPE: protein (xi) SEQUENCE DESCRIPTION: SEQ ID NO:3:

```
Met Ala Ala Phe Ser Lys Tyr Leu Thr Ala Arg Asn Ser Ser Leu Ala
1               5                   10                  15

Gly Ala Ala Phe Leu Leu Leu Cys Leu Leu His Lys Arg Arg Arg Ala
            20                  25                  30

Leu Gly Leu His Gly Lys Lys Ser Gly Lys Pro Pro Leu Gln Asn Asn
        35                  40                  45

Glu Lys Glu Gly Lys Lys Glu Arg Ala Val Val Asp Lys Val Phe Phe
    50                  55                  60

Ser Arg Leu Ile Gln Ile Leu Lys Ile Met Val Pro Arg Thr Phe Cys
65                  70                  75                  80

Lys Glu Thr Gly Tyr Leu Val Leu Ile Ala Val Met Leu Val Ser Arg
                85                  90                  95

Thr Tyr Cys Asp Val Trp Met Ile Gln Asn Gly Thr Leu Ile Glu Ser
            100                 105                 110

Gly Ile Ile Gly Arg Ser Arg Lys Asp Phe Lys Arg Tyr Leu Leu Asn
        115                 120                 125

Phe Ile Ala Ala Met Pro Leu Ile Ser Leu Val Asn Asn Phe Leu Lys
    130                 135                 140

Tyr Gly Leu Asn Glu Leu Lys Leu Cys Phe Arg Val Arg Leu Thr Lys
145                 150                 155                 160

Tyr Leu Tyr Glu Glu Tyr Leu Gln Ala Phe Thr Tyr Tyr Lys Lys Gly
                165                 170                 175

Asn Leu Asp Asn Arg Ile Ala Asn Pro Asp Gln Leu Leu Thr Gln Asp
            180                 185                 190

Val Glu Lys Phe Cys Asn Ser Val Val Asp Leu Tyr Ser Asn Leu Ser
        195                 200                 205

Lys Pro Phe Leu Asp Ile Val Leu Tyr Ile Phe Lys Leu Thr Ser Ala
    210                 215                 220

Ile Gly Ala Gln Gly Pro Ala Ser Met Met Ala Tyr Leu Val Val Ser
225                 230                 235                 240

Gly Leu Phe Leu Thr Arg Leu Arg Arg Pro Ile Gly Lys Met Thr Ile
                245                 250                 255

Thr Glu Gln Lys Tyr Glu Gly Glu Tyr Arg Tyr Val Asn Ser Arg Leu
            260                 265                 270

Ile Thr Asn Ser Glu Glu Ile Ala Phe Tyr Asn Gly Asn Lys Arg Glu
        275                 280                 285

Lys Gln Thr Val His Ser Val Phe Arg Lys Leu Val Glu His Leu His
    290                 295                 300

Asn Phe Ile Leu Phe Arg Phe Ser Met Gly Phe Ile Asp Ser Ile Ile
305                 310                 315                 320

Ala Lys Tyr Leu Ala Thr Val Val Gly Tyr Leu Val Val Ser Arg Pro
                325                 330                 335

Phe Leu Asp Leu Ser His Pro Arg His Leu Lys Ser Thr His Ser Glu
            340                 345                 350

Leu Leu Glu Asp Tyr Tyr Gln Ser Gly Arg Met Leu Leu Arg Met Ser
        355                 360                 365

Gln Ala Leu Gly Arg Ile Val Leu Ala Gly Arg Glu Met Thr Arg Leu
    370                 375                 380
```

```
Ala Gly Phe Thr Ala Arg Ile Thr Glu Leu Met Gln Val Leu Lys Asp
385                 390                 395                 400

Leu Asn His Gly Lys Tyr Glu Arg Thr Met Val Ser Gln Gln Glu Lys
            405                 410                 415

Gly Ile Glu Gly Val Gln Val Ile Pro Leu Ile Pro Gly Ala Gly Glu
        420                 425                 430

Ile Ile Ile Ala Asp Asn Ile Ile Lys Phe Asp His Val Pro Leu Ala
        435                 440                 445

Thr Pro Asn Gly Asp Val Leu Ile Arg Asp Leu Asn Phe Glu Val Arg
    450                 455                 460

Ser Gly Ala Asn Val Leu Ile Cys Gly Pro Asn Gly Cys Gly Lys Ser
465                 470                 475                 480

Ser Leu Phe Arg Val Leu Gly Glu Leu Trp Pro Leu Phe Gly Gly Arg
            485                 490                 495

Leu Thr Lys Pro Glu Arg Arg Lys Leu Phe Tyr Val Pro Gln Arg Pro
            500                 505                 510

Tyr Met Thr Leu Gly Thr Leu Arg Asp Gln Val Ile Tyr Pro Asp Gly
    515                 520                 525

Arg Glu Asp Gln Lys Arg Lys Gly Ile Ser Asp Leu Val Gln Lys Glu
    530                 535                 540

Tyr Leu Asp Asn Val Gln Leu Gly His Ile Leu Glu Arg Glu Gly Gly
545                 550                 555                 560

Trp Asp Ser Val Gln Asp Trp Met Asp Val Leu Ser Gly Gly Glu Lys
            565                 570                 575

Gln Arg Met Ala Met Ala Arg Leu Phe Tyr His Lys Pro Gln Phe Ala
            580                 585                 590

Ile Leu Asp Glu Cys Thr Ser Ala Val Ser Val Asp Val Glu Gly Tyr
    595                 600                 605

Ile Tyr Ser His Cys Arg Lys Val Gly Ile Thr Leu Phe Thr Val Ser
    610                 615                 620

His Arg Lys Ser Leu Trp Lys His His Glu Tyr Tyr Leu His Met Asp
625                 630                 635                 640

Gly Arg Gly Asn Tyr Glu Phe Lys Gln Ile Thr Glu Asp Thr Val Glu
                645                 650                 655

Phe Gly Ser (2) INFORMATION FOR SEQ ID NO:4:

(i) SEQUENCE CHARACTERISTICS:
        (A) LENGTH: 152 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

AGGTGGGGCA GGTTGGGGTG CCGGGCACGG AGGGAAGCGT GTGGCAGGGA GGCCCGGGGG      60

CAGGCAGCCG TGAGCGGTGG GGACAGTCTG GGGCGGGCCG GGGCTGATGC CAAAGGTGTG     120

GGCAGGCCAT GGGAGAGCCG GGCTGGGGTG GG                                   152

(2) INFORMATION FOR SEQ ID NO:5:

(i) SEQUENCE CHARACTERISTICS:
        (A) LENGTH: 152 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:5:

CACCCAATCG TAACCTCTGG CTCTCGGCCT TCTGATGGCC ACCATGGCAC AGCGTGTGTG     60

AGTGGCACTG GGAGACCCTG ACCATCGCCC CCACGGGAGC TGCCCCTGTG CATGGCCAGG    120

AAGCCTCTCT GTGTCTGTCA CCCCCCGCAG GT                                 152

(2) INFORMATION FOR SEQ ID NO:6:

(i) SEQUENCE CHARACTERISTICS:
            (A) LENGTH: 152 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:6:

AGGTGAGACC CAGGGCTCCA AGAGGATCCA GGCCAGGGGC CTGTCCCCCA TACCGCTGGG     60

TGCTGAGCTC ACGAGGGCCC AACTCAGCCA GCCCGCCGCC CACTTCTGCT GCCGGGGCCA    120

CCGAGGCCCT GCTGCCAGCC TTGATGCTTT CA                                 152

(2) INFORMATION FOR SEQ ID NO:7:

(i) SEQUENCE CHARACTERISTICS:
            (A) LENGTH: 152 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:7:

GCACATAGAG AGAAAGAGAG AGAGAGCTGG TTGCCCCGGC ACCATTTGCA GAAGAGCCTC     60

GCCTTTCTCT CCAGCGGCTC ATTTTTGACT TTCCGCTGTC TCTGCCCTGC CCCTCCCCGC    120

CCCGCCACCC ACCCCTCTGG GGCTTTGCAG AT                                 152

(2) INFORMATION FOR SEQ ID NO:8:

(i) SEQUENCE CHARACTERISTICS:
            (A) LENGTH: 97 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:8:

AGGAGGTACC CCTGGCCCAG CCCCACCCTT GCCATCCTTG CCATGCTTCT CTCCCTGCAA     60

CTGGCAGGGG CTGAGCCAGG GTCACCCTCC CTCAGGT                             97

(2) INFORMATION FOR SEQ ID NO:9:

(i) SEQUENCE CHARACTERISTICS:
            (A) LENGTH: 152 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:9:

AGGTAAGGCT GTCCCCTCCC TATGAGTGAC CCCGCCCCTG CTGCTGCTGC AGGTGCTGAC     60

```
CTGCTGCCCC AGCTCCTCCT ATTCCCGCTC CCTCACTCAG GGACCTCCAT GTGCTTCTGG      120

CCCATCCCAG TCCACCCAGG ACGGGAGGGC TG                                   152

(2) INFORMATION FOR SEQ ID NO:10:

(i) SEQUENCE CHARACTERISTICS:
          (A) LENGTH: 152 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:10:

CTGGACCACA GGCTGCTGGT CAGGAACCAG CTGGCATGCT GCCAGGGATG GGAATGAGGG      60

CGTGCAGCCA GGGGCACGCA GACTCCCCAG AATGCAGAGG GGTCGCCACC ACTCCCTCTC     120

CACCCCAGCC CCGCTGTGCT GTCTCTGCAG GC                                   152

(2) INFORMATION FOR SEQ ID NO:11:

(i) SEQUENCE CHARACTERISTICS:
          (A) LENGTH: 152 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:11:

GGGTAGGTCC AGCGGGGAGG GCGCCAGCCA CGCACATATG CAAGCCTCAG CCCTTGGCTT      60

CCCGCCTGTC TGTGCTGGCA ACAGCCATTG TCCCTAGATG TACGTGGCAG GTGGGCCAAG    120

GTCAAGGTGA GAGACCAACG TGTCTCTGAC TG                                   152

(2) INFORMATION FOR SEQ ID NO:12:

(i) SEQUENCE CHARACTERISTICS:
          (A) LENGTH: 152 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:12:

TCCCCCAGGC CCTGCTGTCC CTTATCAAGA GATCAAGAAT GGCCTGCGTG CTGGCCTCGG      60

GCATTGGGAG CCTCTCAAGG CTGGTCAGGA GGCCATAGGG TACGGGAAGG GGCCTGCGCT    120

CTCTGGCGTC AGCGGCTGTT GCCCCTGCAG GT                                   152

(2) INFORMATION FOR SEQ ID NO:13:

(i) SEQUENCE CHARACTERISTICS:
          (A) LENGTH: 340 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:13:

AGGTAAGGAA GCCCGTGCGC CTCTCCTCCA CCTCTTCCTG CCTGTGCGCT CACACATGGC      60

TTCCTGCAGA GGCCCAGGAA GTGGTGAAGA GTCAGCACCT CAGGAGAGGA CACTGAGGCA    120

CTGTCCCCAG AGCCAGAGAC GGGCTGTGGT TCCTGCTCCC TCCAAACCCG CCCGATCCAC    180
```

```
TGCCCTGTTT TGGATCTGTG TGGGGTGTGT GCACGGGCGG CGATGTGAGC GTGTGGATGC      240

GTGTGAGCGT GGCATGTGGA CACTGCCTGG GAGGCGCAGA GTATCTTGGG GGAGGCAGAG      300

CCGGCCCTTC CCTCCGTGGA CACCCAGCTT TCCCACAGGC                            340

(2) INFORMATION FOR SEQ ID NO:14:

(i) SEQUENCE CHARACTERISTICS:
         (A) LENGTH: 152 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:14:

AGGTAGGAGG CCTGGGGCTG GCAGCCACCC TTTGTCCCAC CCTGGCCTCT CCCTTGGCCT       60

CCAGGGAGTG AAGATTACCT CAACATCCAG AGTCTAAAGT GCCAGGTGCC ACGGGGCGGG      120

GCAGAGGCTG CTACCAGGGA GGACCAACAC CA                                   152

(2) INFORMATION FOR SEQ ID NO:15:

(i) SEQUENCE CHARACTERISTICS:
         (A) LENGTH: 152 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:15:

ATGATTAATG CCTGTCAGAC AGACAAGGAC GCAGAGGCAC AGGGGCCCTG TCGTCACAGC       60

TAGCTCATTC CCGCAGCTCC CCCAGCTCCC CGGCTGGCCC CCGGGTCTGG GTGCTGGTGG      120

AACTGAGCCA AGACCATTGC CCCCGCCTAG GT                                   152

(2) INFORMATION FOR SEQ ID NO:16:

(i) SEQUENCE CHARACTERISTICS:
         (A) LENGTH: 153 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:16:

AGGTGAGCAC TCCGGACCGG CAGGCTCCCT GGGGTCCCCT GGAAGGGGAA GTAGCAGCTG       60

TGGGGAGGCC TGGGCTCAGT GGAGCCTGAG CCGGGCTGGG GTGTTGGGCC CTGGAGGGTG      120

CACAGACTCT CCTCTCGGCC CGGACCCCCA GGC                                  153

(2) INFORMATION FOR SEQ ID NO:17:

(i) SEQUENCE CHARACTERISTICS:
         (A) LENGTH: 146 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:17:

TGGTAGGTGC CCTGTCTCCC TGCCTGGGGT CGGTGGGAGT GCCTGCCTGA GGGGAGGAGG       60

TGGCCTGGCG GGCCCGGCAG CAGCAGGCGG CTGTCATCAG CAGCCCCCGT GCCGTGCCCC      120
```

```
TGACCCTGTC CCTCTCCTGG CCAGGA                                          146
```

(2) INFORMATION FOR SEQ ID NO:18:

(i) SEQUENCE CHARACTERISTICS:
        (A) LENGTH: 1441 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

```
GCGGAGCGGA CGGACGCGCC TGGTGCCCCG GGGAGGGGCG CCACCGGGGG AGGAGGAGGA     60
GGAGAAGGTG GAGAGGAAGA GACGCCCCCT CTGCCCGAGA CCTCTCAAGG CCCTGACCTC    120
AGGGGCCAGG GCACTGACAG GACAGGAGAG CCAAGTTCCT CCACTTGGGC TGCCCGAAGA    180
GGCCGCGACC CTGGAGGGCC CTGAGCCCAC CGCACCAGGG GCCCCAGCAC CACCCCGGGG    240
GCCTAAAGCG ACAGTCTCAG GGGCCATCGC AAGGTTTCCA GTTGCCTAGA CAACAGGCCC    300
AGGGTCAGAG CAACAATCCT TCCAGCCACC TGCCTCAACT GCTGCCCCAG GCACCAGCCC    360
CAGTCCCTAC GCGGCAGCCA GCCCAGGTGA CATGCCGGTG CTCTCCAGGC CCCGGCCCTG    420
GCGGGGGAAC ACGCTGAAGC GCACGGCCGT GCTCCTGGCC CTCGCGGCCT ATGGAGCCCA    480
CAAAGTCTAC CCCTTGGTGC GCCAGTGCCT GGCCCCGGCC AGGGGTCTTC AGGCGCCCGC    540
CGGGGAGCCC ACGCAGGAGG CCTCCGGGGT CGCGGCGGCC AAAGCTGGCA TGAACCGGGT    600
ATTCCTGCAG CGGCTCCTGT GGCTCCTGCG GCTGCTGTTC CCCCGGGTCC TGTGCCGGGA    660
GACGGGGCTG CTGGCCCTGC ACTCGGCCGC CTTGGTGAGC CGCACCTTCC TGTCGGTGTA    720
TGTGGCCCGC CTGGACGGAA GGCTGGCCCG CTGCATCGCC CGCAAGGACC CGCGGGCTTT    780
TGGCTGGCAG CTGCTGCAGT GGCTCCTCAT CGCCCTCCCT GCTACCTTCG TCAACAGTGC    840
CATCCGTTAC CTGGAGGGCC AACTGGCCCT GTCGTTCCGC AGCCGTCTGG TGGCCCACGC    900
CTACCGCCTC TACTTCTCCC AGCAGACCTA CTACCGGGTC AGCAACATGG ACGGGCGGCT    960
TCGCAACCCT GACCAGTCTC TGACGGAGGA CGTGGTGGCC TTTGCGGCCT CTGTGGCCCA   1020
CCTCTACTCC AACCTGACCA AGCCACTCCT GGACGTGGCT GTGACTTCCT ACACCCTGCT   1080
TCGGGCGGCC CGCTCCCGTG GAGCCGGCAC AGCCTGGCCC TCGGCCATCG CCGGCCTCGT   1140
GGTGTTCCTC ACGGCCAACG TGCTGCGGGC CTTCTCGCCC AAGTTCGGGG AGCTGGTGGC   1200
AGAGGAGGCG CGGCGGAAGG GGGAGCTGCG CTACATGCAC TCGCGTGTGG TGGCCAACTC   1260
GGAGGAGATC GCCTTCTATG GGGCCATGA GGTGGGGCAG GTTGGGGTGC CGGGCACGGA   1320
GGGAAGCGTG TGGCAGGGAG GCCCGGGGGC AGGCAGCCGT GAGCGGTGGG GACAGTCTGG   1380
GGCGGGCCGG GGCTGATGCC AAAGGTGTGG GCAGGCCATG GGAGAGCCGG GCTGGGGTGG   1440
G                                                                  1441
```

(2) INFORMATION FOR SEQ ID NO:19:

(i) SEQUENCE CHARACTERISTICS:
        (A) LENGTH: 481 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

```
CACCCAATCG TAACCTCTGG CTCTCGGCCT TCTGATGGCC ACCATGGCAC AGCGTGTGTG     60
```

```
AGTGGCACTG GGAGACCCTG ACCATCGCCC CCACGGGAGC TGCCCCTGTG CATGGCCAGG        120

AAGCCTCTCT GTGTCTGTCA CCCCCCGCAG GTGGAGCTGG CCCTGCTACA GCGCTCCTAC        180

CAGGACCTGG CCTCGCAGAT CAACCTCATC CTTCTGGAAC GCCTGTGGTA TGTTATGCTG        240

GAGCAGTTCC TCATGAAGTA TGTGTGGAGC GCCTCGGGCC TGCTCATGGT GGCTGTCCCC        300

ATCATCACTG CCACTGGCTA CTCAGAGTCA GGTGAGACCC AGGGCTCCAA GAGGATCCAG        360

GCCAGGGGCC TGTCCCCCAT ACCGCTGGGT GCTGAGCTCA CGAGGGCCCA ACTCAGCCAG        420

CCCGCCGCCC ACTTCTGCTG CCGGGGCCAC CGAGGCCCTG CTGCCAGCCT TGATGCTTTC        480

A                                                                      481

(2) INFORMATION FOR SEQ ID NO:20:

(i) SEQUENCE CHARACTERISTICS:
        (A) LENGTH: 702 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GCACATAGAG AGAAAGAGAG AGAGAGCTGG TTGCCCCGGC ACCATTTGCA GAAGAGCCTC         60

GCCTTTCTCT CCAGCGGCTC ATTTTTGACT TTCCGCTGTC TCTGCCCTGC CCCTCCCCGC        120

CCCGCCACCC ACCCCTCTGG GGCTTTGCAG ATGCAGAGGC CGTGAAGAAG GCAGCCTTGG        180

AAAAGAAGGA GGAGGAGCTG GTGAGCGAGC GCACAGAAGC CTTCACTATT GCCCGCAACC        240

TCCTGACAGC GGCTGCAGAT GCCATTGAGC GGATCATGTC GTCGTACAAG GAGGTACCCC        300

TGGCCCAGCC CCACCCTTGC CATCCTTGCC ATGCTTCTCT CCCTGCAACT GGCAGGGGCT        360

GAGCCAGGGT CACCCTCCCT CAGGTGACGG AGCTGGCTGG CTACACAGCC CGGGTGCACG        420

AGATGTTCCA GGTATTTGAA GATGTTCAGC GCTGTCACTT CAAGAGGCCC AGGGAGCTAG        480

AGGACGCTCA GGCGGGGTCT GGGACCATAG GCCGGTCTGG TGTCCGTGTG GAGGGCCCCC        540

TGAAGATCCG AGGTAAGGCT GTCCCCTCCC TATGAGTGAC CCCGCCCCTG CTGCTGCTGC        600

AGGTGCTGAC CTGCTGCCCC AGCTCCTCCT ATTCCCGCTC CCTCACTCAG GGACCTCCAT        660

GTGCTTCTGG CCCATCCCAG TCCACCCAGG ACGGGAGGGC TG                          702

(2) INFORMATION FOR SEQ ID NO:21:

(i) SEQUENCE CHARACTERISTICS:
        (A) LENGTH: 395 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

CTGGACCACA GGCTGCTGGT CAGGAACCAG CTGGCATGCT GCCAGGGATG GGAATGAGGG         60

CGTGCAGCCA GGGGCACGCA GACTCCCCAG AATGCAGAGG GGTCGCCACC ACTCCCTCTC        120

CACCCCAGCC CCGCTGTGCT GTCTCTGCAG GCCAGGTGGT GGATGTGGAA CAGGGGATCA        180

TCTGCGAGAA CATCCCCATC GTCACGCCCT CAGGAGAGGT GGTGGTGGCC AGCCTCAACA        240

TCAGGGTAGG TCCAGCGGGG AGGGCGCCAG CCACGCACAT ATGCAAGCCT CAGCCCTTGG        300

CTTCCCGCCT GTCTGTGCTG GCAACAGCCA TTGTCCCTAG ATGTACGTGG CAGGTGGGCC        360

AAGGTCAAGG TGAGAGACCA ACGTGTCTCT GACTG                                  395
```

(2) INFORMATION FOR SEQ ID NO:22:

(i) SEQUENCE CHARACTERISTICS:
        (A) LENGTH: 928 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

```
TCCCCCAGGC CCTGCTGTCC CTTATCAAGA GATCAAGAAT GGCCTGCGTG CTGGCCTCGG      60
GCATTGGGAG CCTCTCAAGG CTGGTCAGGA GGCCATAGGG TACGGGAAGG GGCCTGCGCT     120
CTCTGGCGTC AGCGGCTGTT GCCCCTGCAG GTGGAGGAAG GCATGCATCT GCTCATCACA     180
GGCCCCAATG GCTGCGGCAA GAGCTCCCTG TTCCGGATCC TGGGTGGGCT CTGGCCCACG     240
TACGGTGGTG TGCTCTACAA GCCCCCACCC CAGCGCATGT TCTACATCCC GCAGAGGTAA     300
GGAAGCCCGT GCGCCTCTCC TCCACCTCTT CCTGCCTGTG CGCTCACACA TGGCTTCCTG     360
CAGAGGCCCA GGAAGTGGTG AAGAGTCAGC ACCTCAGGAG AGGACACTGA GGCACTGTCC     420
CCAGAGCCAG AGACGGGCTG TGGTTCCTGC TCCCTCCAAA CCCGCCCGAT CCACTGCCCT     480
GTTTTGGATC TGTGTGGGGT GTGTGCACGG GCGGCGATGT GAGCGTGTGG ATGCGTGTGA     540
GCGTGGCATG TGGACACTGC CTGGGAGGCG CAGAGTATCT TGGGGGAGGC AGAGCCGGCC     600
CTTCCCTCCG TGGACACCCA GCTTTCCCAC AGGCCCTACA TGTCTGTGGG CTCCCTGCGT     660
GACCAGGTGA TCTACCCGGA CTCAGTGGAG GACATGCAAA GGAAGGGCTA CTCGGAGCAG     720
GACCTGGAAG CCATCCTGGA CGTCGTGCAC CTGCACCACA TCCTGCAGCG GGAGGGAGGT     780
AGGAGGCCTG GGGCTGGCAG CCACCCTTTG TCCCACCCTG GCCTCTCCCT TGGCCTCCAG     840
GGAGTGAAGA TTACCTCAAC ATCCAGAGTC TAAAGTGCCA GGTGCCACGG GGCGGGGCAG     900
AGGCTGCTAC CAGGGAGGAC CAACACCA                                       928
```

(2) INFORMATION FOR SEQ ID NO:23:

(i) SEQUENCE CHARACTERISTICS:
        (A) LENGTH: 1025 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

```
ATGATTAATG CCTGTCAGAC AGACAAGGAC GCAGAGGCAC AGGGGCCCTG TCGTCACAGC      60
TAGCTCATTC CCGCAGCTCC CCCAGCTCCC CGGCTGGCCC CCGGGTCTGG GTGCTGGTGG     120
AACTGAGCCA AGACCATTGC CCCCGCCTAG GTTGGGAGGC TATGTGTGAC TGGAAGGACG     180
TCCTGTCGGG TGGCGAGAAG CAGAGAATCG GCATGGCCCG CATGTTCTAC CACAGGTGAG     240
CACTCCGGAC CGGCAGGCTC CCTGGGGTCC CCTGGAAGGG GAAGTAGCAG CTGTGGGGAG     300
GCCTGGGCTC AGTGGAGCCT GAGCCGGGCT GGGGTGTTGG GCCCTGGAGG GTGCACAGAC     360
TCTCCTCTCG GCCCGGACCC CCAGGCCCAA GTACGCCCTC CTGGATGAAT GCACCAGCGC     420
CGTGAGCATC GACGTGGAAG GCAAGATCTT CCAGGCGGCC AAGGACGCGG GCATTGCCCT     480
GCTCTCCATC ACCCACCGGC CCTCCCTGTG GTAGGTGCCC TGTCTCCCTG CCTGGGGTCG     540
GTGGGAGTGC CTGCCTGAGG GGAGGAGGTG GCCTGGCGGG CCCGGCAGCA GCAGGCGGCT     600
GTCATCAGCA GCCCCCGTGC CGTGCCCCTG ACCCTGTCCC TCTCCTGGCC AGGAAATACC     660
```

-continued

```
ACACACACTT GCTACAGTTC GATGGGGAGG GCGGCTGGAA GTTCGAGAAG CTGGACTCAG    720

CTGCCCGCCT GAGCCTGACG GAGGAGAAGC AGCGGCTGGA GCAGCAGCTG GCGGGCATTC    780

CCAAGATGCA GCGGCGCCTC CAGGAGCTCT GCCAGATCCT GGGCGAGGCC GTGGCCCCAG    840

CGCATGTGCC GGCACCTAGC CCGCAAGGCC CTGGTGGCCT CCAGGGTGCC TCCACCTGAC    900

ACAACCGTCC CCGGCCCCTG CCCCGCCCCC AAGCTCGGAT CACATGAAGG AGACAGCAGC    960

ACCCACCCAT GCACGCACCC CGCCCCTGCA TGCCTGGCCC CTCCTCCTAG AAAACCCTTC   1020

CCGCC                                                               1025
```

X-LINKED ADRENOLEUKODYSTROPHY GENE AND CORRESPONDING PROTEIN

This application is a division of application Ser. No. 08/136,277, filed Oct. 15, 1993 now U.S. Pat. No. 5,644,045.

BACKGROUND OF THE INVENTION

The present application relates to the identification and isolation of a gene which is responsible for the adrenoleukodystrophy. It further concerns the protein encoded by this gene and their use in diagnostic or therapeutic procedures.

Adrenoleukodystrophy (ALD) is an X-linked disease affecting 1/20,000 males either as cerebral ALD in childhood or as adrenomyleneuropathy (AMN) in adults. Childhood ALD is the more severe form, with onset of neurological symptoms between 5–12 years of age. Central nervous system demyelination progresses rapidly and death occurs within a few years. AMN is a milder form of the disease with onset at 15–30 years of age and a more progressive course. Adrenal insufficiency (Addison's disease) may remain the only clinical manifestation of ALD. The principal biochemical abnormality of ALD is the accumulation of very long chain fatty acids (VLCFA) because of impaired β-oxidation in peroxisomes. The normal oxidation of VLCFA-CoA in patients fibroblasts suggested that the gene coding for the VLCFA-CoA synthetase could be a candidate gene for ALD.

ALD or its variant AMN is a monogenic disease but its clinical expression can be under the control of several genes or factors, leading to phenotypic variability.

Adrenoleukodystrophy and adrenomyeloneuropathy are characterized by the presence of an abnormal ALD gene, resulting from deletions or other types of mutations including point mutations. The mutations in the gene may nevertheless remain clinically silent or may lead to various phenotypic clinical expression.

Although it was known that the gene responsible for the adrenoleukodystrophy is located on the Xq28 region of the X chromosome, the results which have been described up to now have not permitted to identify and characterize the gene responsible for the ALD.

Some experiments were for instance conducted in order to check any possible relationship between the alteration of the gene responsible for the colour vision and the ALD gene. The inventors have now shown that although these genes of the red/green colour pigment also map to the Xq28 region, they are not linked either structurally or functionally to the ALD gene.

For the purpose of this description, it is mentioned that expression "ALD gene" encompasses the gene involved in ALD and also in its adult variant AMN.

SUMMARY OF THE INVENTION

The invention accordingly relates to an isolated nucleotide sequence which is for instance selected among DNA, RNA, cDNA sequences, responsible for the adrenoleukodystrophy or the adrenomyeloneuropathy.

By the expression "sequences responsible for ALD or AMN" it must be understood that the abnormal form of the ALD gene is involved in the ALD pathology; of course the normal gene (devoid of mutations, especially of deletions) does not cause the disease.

The term "isolation" refers to the fact that the nucleotide sequence is separated from the other nucleotide sequences of the Xq28 region of the X chromosome when it is purified for instance from a natural source or organism. This isolated nucleotide sequence is also obtainable from synthetic or semi-synthetic sources, according to well-known methods. This sequence can be any type of nucleotide sequence and especially can be selected among DNA, RNA or cDNA.

A particular sequence which is referred to according to the invention consists essentially of the human gene responsible for the ALD. This gene accordingly contains both exons and introns and therefore contains both coding sequences of the gene and regulation sequences.

A preferred embodiment of the invention provides for an isolated nucleotide sequence having the sequence represented on FIG. 6 (SEQ ID NOS:4–17) and FIGS. 7A–7D (SEQ ID NOS:8–23).

The inventors have shown that the gene coding for the ALD protein, contains 10 exons and 9 introns. It must be noted that the deletions and/or mutations which affect the gene and which accordingly are capable of giving rise to the ALD disease or its variant AMN, can be situated either in the exons or in the introns. When these modifications affect the intron sequences, they are often located in the sequence of the intron which is adjacent to the coding sequence. Presence of a mutation in the gene is a condition necessary for the expression of the disease but can remain insufficient to lead to the expression of clinical symptoms related to this disease.

According to another preferred embodiment of the invention, the nucleotide sequence consists of the coding sequence of the gene.

In particular, this coding sequence can be a cDNA corresponding to the sequence represented on FIG. 2 (SEQ ID NO:1).

According to another embodiment of the invention, the isolated DNA sequence is characterised in that it consists essentially of a DNA sequence encoding the human adrenoleukodystrophy protein. In such a case, the DNA sequence codes for the amino-acid sequence represented on FIG. 2.

The invention further relates to nucleotide sequences which are modified regarding the above described sequence but which nevertheless hybridize under stringent conditions defined hereafter with a nucleotide sequence as described above. Such a sequence contains preferably at least 10 nucleotides and has advantageously a length of around 20 to 100, preferably 20 to 50 nucleotides.

A preferred nucleotide sequence of the invention can further be characterized by the restriction map which is given on FIG. 5 or by the structural organization which is also given on FIG. 5.

The invention also concerns nucleotide fragments selected among DNA or cDNA fragments, which contain at least 10 nucleotides and advantageously at least 20 nucleotides, and are capable of hybridizing specifically, with a sequence which has been defined hereabove.

The hybridization is said specific if the nucleotide fragment does not hybridize for instance with the DNA sequence of the human PMP protein or the DNA of other proteins of the ATP binding protein superfamily.

The fragments of the invention can be labelled in order for instance to be used as probes or can be also involved as primers for amplification reactions and especially for PCR reactions.

The probes of the invention are advantageously labelled by any label classically used. They may be labelled with the aid of a radioactive marker such as $^{32}P$, $^{35}S$, $^{125}I$, $^{3}H$, $^{16}C$ and the radioactive labelling may be performed by any method known to the person skilled in the art.

The probes may be labelled at the 3' end by addition of one or more deoxynucleotides or ribonucleotides or by a dideoxynucleotide labelled in the alpha position by means of $^{32}$P, in the presence of the terminal deoxynucleotidyl transferase, or at the 5' end by transfer of a radioactive phosphate group of a free deoxynucleotide or dideoxynucleotide labelled in the gamma position in the presence of the T4 DNA ligase. The probes may also be labelled by using a DNA polymerase by means of "nick translation" or "random priming" or "polymerase chain reaction".

The method of detection of the hybridization will depend on the radioactive label used and may be based on autoradiography, liquid scintillation, gamma counting or any other technique making possible the detection of the radiation emitted by the radioactive label.

Non-radioactive labelling may also be used by combining with the probes groups exhibiting immunological properties such as an antigen, a specific affinity for certain reagents such as a ligand, physical properties such as fluorescence or luminescence, properties making possible the completion of enzymatic reactions such as an enzyme or an enzyme substrate. The non-radioactive labelling may also be performed directly by chemical modification of the DNA, such as photobiotinylation or sulfonation.

A particular fragment which can be used as a probe is the fragment which is designated by "X2" and which corresponds to an XbaI-EcoRI fragment of 1,8 kb included in the sequence represented on FIG. 6.

Other preferred probes are those designated by Ex13 and Ex3 and represented on FIG. 2.

Particularly preferred fragments to be used as primers for amplification procedures are those which are situated within the sensitive parts of the gene, i.e., the parts which may be more susceptible to mutations or deletions, or also fragments which are surrounding these regions.

Interesting primers are for instance those corresponding to sequences extending from position 1,853 to position 1,872 or from position 1,854 to position 1,874 or from position 2,357 to position 2,375 as shown on FIG. 2 (SEQ ID NO:1).

The diagnosis can be made to detect the anomaly of the gene in patients presenting clinical symptoms of the disease or unaffected persons capable of transmitting the disease, especially in women carriers or as a neonatal screening.

The invention also concerns a pharmaceutical composition comprising an isolated nucleotide sequence according to the definitions given above, together with a physiological acceptable pharmaceutical vehicle.

A particularly useful pharmaceutical composition is one which contains the genomic DNA of the ALD gene or the cDNA corresponding thereto.

Another aspect of the invention relates to a protein consisting essentially of the adrenoleukodystrophy protein.

In a preferred embodiment, this protein is characterized by the amino-acid sequence given in FIG. 2 (SEQ ID NO:2).

The invention also relates to a protein having a sufficient homology with the amino-acid sequence given above, to have the essential biological properties of the ALD protein.

These biological properties are the ability to complement the biological defect in cells from patients with ALD or AMN, or to share immunological determinants (epitopes) with the ALD protein.

Another protein within the scope of the invention has the essential biological properties described above and is such that the 52 amino-acid residues of its C-terminal end have an homology of at least 75%, preferably 80% and more preferably 90% with the aligned amino-acid sequence which has been given above.

The invention also relates to amino-acid fragments or sequences containing at least 7 amino-acid residues, which fragments are recognized by antibodies that bind specifically the protein of the invention.

Preferred fragments contain from 7 to around 745 or 500 amino-acids, advantageously from 7 to around 100, preferably from 7 to around 50 and most preferably from 7 to around 20.

Particular amino-acid sequences are derived from regions of the sequence represented on FIG. 2, which are specific for the ALD protein and especially which are not common to sequences of human and rat 70 KPMP protein and other members of the ATP binding protein superfamily, such as those described in the publication of Mosser J. et al (Nature, vol. 361, Feb. 25, 1993, pages 726–730).

The antibodies capable of binding preferably specifically the ALD protein of the invention, especially monoclonal antibodies are obtained according to usual methods, involving the production of hybridoma cells, formed by fusion of spleen cells of an animal previously immunized with a protein of the invention and myeloma cells.

Specific monoclonal antibodies detect a protein having an apparent molecular weight of 75 kDa.

The invention further encompasses the antibodies, either monoclonal or polyclonal that bind specifically the protein according to the above definition.

The specific binding can be checked by assaying these antibodies with proteins having homologies with the ALD protein, for instance with the rat or human 70 peroxisomal membrane protein (PMP) or other proteins of the ATP binding protein superfamily as cited above. The antibodies of the invention are those which do not bind these different proteins presenting some homology with the ALD protein.

The nucleotide sequence or protein or fragments thereof of the invention are useful for diagnostic or therapeutic purposes.

Especially the nucleotide sequences or fragments as defined above can be used in a process for the in vitro diagnosis of the ALD or AMN disease in a human patient, these sequences being used as probes or as primers.

Usual techniques like those which are involved in the detection of genetic diseases are for instance southern blotting RFLP (Restriction Fragment Length Polymorphism) detection or PCR reactions.

The detection of the protein can be performed using specific antibodies, monoclonal or polyclonal.

The detection is performed on samples containing for instance blood cells.

In the present case due to the possibility of various mutations of the ALD gene, it can be useful to have recourse to multiplex PCR, using different primers for amplification of several regions of the gene.

The invention also relates to a process for the treatment of cells and especially somatic cells of a human patient affected by ALD or AMN, comprising the administration to the patient of cells previously modified with a nucleotide sequence as described above. The cells can be modified by recombinant nucleotide sequences containing one of the DNA, cDNA or RNA sequence of the invention, under the control of regulation elements in a vector appropriate for the modification or transfection of cells. Advantageously the regulation elements are capable of ensuring a high level of expression and comprise accordingly strong promoters, possibly an enhancer and in some instances a reporter gene such as for example the neo gene or the dhfr gene.

Appropriate vectors can be plasmid vectors, retroviruses vectors or for instance adenoviruses vectors.

The transfer of the sequence useful for therapeutic purposes is performed by ex vivo techniques like electroporation, transfection especially calcium phosphate transfection or fusion for instance with liposomes.

The somatic transfer can also be performed in vivo using cells as vectors, which cells are previously modified ex vivo with the gene of interest. Accordingly hematopoietic cells or nervous cells are used. Among the techniques which are available for in vivo transfer of gene one can further cite inert vectors like liposomes, viral vectors, especially retroviruses or adenoviruses or directly by injection of DNA.

The vectors used for the somatic transfer of the gene or sequences of the invention can also be directly transfered in vivo, for instance by direct injection in the blood stream or by stereotactic injection in specific regions of the brain (Stratlford-Perricaudet LD et al J Clin Invest 90,626–630. Akli S et al Nature genomics vol 3, March 1993).

The direct administration of DNA has been described for instance by Wolff J. A. et al (1990, Science 247, 1465–1468) or Acsadi G. et al (1991, Nature 352, 815–818).

As example, for the preparation of the vector, the sequence of the ALD gene, preferably the cDNA corresponding to the ALD gene is inserted in a defective murine Moloney vector (Mo-MLV), under the control of regulation elements. The defective vector still contains its cis-sequences such as the LTR sequence or part thereof sufficient for the transcription and integration, the psi sequence necessary for the encapsidation and the PB sequence for viral replication. In this vector the viral genes gag, pol, env are at least partly deleted and substituted with the sequence of interest. This sequence is placed under the control of its own promoter or a stronger promoter such as the SV40 promoter. A marker gene is possibly added to the construction.

The helper virus used contains the retroviral genes (gag, pol, env) necessary for replication of the viral genome and for the formation of the viral particles. To the contrary the cis-sequences which are present in the vector are deleted in the helper virus.

The helper provirus is inserted in a murine cell line especially NIH/3T3 as host.

The vector is then transfected in the cell line allowing the production of viral particles.

From a general point of view, the techniques used for the transfer of the human ADA gene (Adenosine desaminase) in cells can be also used in the present situation. Like the ADA gene, the ALD gene or its cDNA is transfected with a retrovirus in fibroblast cells (Palmer et al. PNAS, 1987, 84, 1055–1059), or in lymphocytes or other hematopoietic cells including precursor or stem cells (Culver et al. Hum Gene Ther 2,107 1991 or Anderson WF Science vol 256 May 6 1992 p808)

Other characteristics and advantages of the invention will become apparent from the examples and figures.

BRIEF DESCRIPTION OF DRAWINGS

FIGS. 1A and 1B Map of the ALD gene region and its rearrangements in patients. a, chromosomal rearrangement in patient O. The joining of BP4-BP2 and BP3-BP1 were demonstrated by cloning the corresponding junction fragments (dashed lines). The extends of the two deletions (19.2 and 88 kb respectively) are indicated in b. Probe X2 (circle) is discussed in the examples and other probes (filled circles, Fr probes) are from Martinez, C. M. et al, (Cell Biol. int. Rep. 14, 255–266, 1990). The distance between probes Fr14 and Fr11 (broken line) is not known. The green cone pigment gene (GCP) is indicated by a box (G). b, Map of the R/GCP genes and of the second deletion in patient O, including the rare cutter restriction sites (vertical bars, top) EagI (Ea), BsaHIT (Bs), SacIt (S), ClaT (C), NotT (N) and MluT (M). The rare cutter sites within the pigment gene repeat unit are not marked. The extents of the two deletions (wavy lines) and the position of the 4 BPs in patient O are indicated. Probe Fr15.4 (deleted in patient O) was used to screen a Xq28-specific cosmid library, yielding 3 overlapping clones (cos Qc 11H12, cos Qc 8F3 and cos Qc 14A11). The red cone pigment (RCP) gene is indicated by the filed box (R) and the GCP bene by a box (G. c, Deletions detected in 5 ALD patients and restriction map of the subcloned region of ALD gene using the following enzymes: EcoRI (E), HINDIII (H), BamHI (B), and XhaI (X). Rare cutter sites are indicated as in b. Localization of subcloned probe is shown at the top. Probe X2 (box) is a 1.8 kb XhaI-EcoRT restriction fragment derived form X-8, the second junction fragment (BP4-BP2) in patient O. TA25 (2.1 kb), Ta4 (3.6 kb), Ta1 (1.0 kb), Ta18 (0.85 kb), Ta13a (935 bp) and Ta13b (252 bp) are TaqI-digested DNA fragments (hatched boxes) derived from subcloning of cosmid Qc 11H12. d, Segregation of an abnormal junction fragment detected by probe X2 in ALD family B. Probe X2 hybridizes to a 16-kb HindIII fragment in normal individuals (open square and circle). An abnormal 14.4-kb junction fragment was detected in an affected ALD patient (patient B; see panel c) and in all heterozygous females. e, Detection of the same rearranged DNA fragment in two ALD brothers with different clinical ALD phenotypes by Southern blot analysis of HindI1I-digested DNA from 3 brothers (Family Ma; sec c) hybridized with probe X2. An abnormal junction fragment of 22 kb is detected by X2 in a male with cerebral ALD (filled square) and his brother with Addison's disease (hatched square). METHODS. Restriction patterns of the cosmids were analysed as described. Cosmid Qc 11H12 was digested with TaqI and cloned directly in the ClaI site of pBluescript SK$^+$ (Stratagene). X-8 was isolated from a XbaI genomic library constructed in bacteriophage λ (Stratagene) using DNA from a somatic hybrid line containing the X chromosome of patient O. Gel electrophoresis, Southern blotting, probing and autoradiography were all done as described.

FIGS. 2A–2B Sequence of ALD-protein cDNA (SEQ ID NOS:1 and 2). The sequence is derived from analysis of clones obtained by exon connection and clones isolated from a HoLa cDNA library, and confirmed in most cases by sequences of genomic clones. METHODS. Four probes (Ta25, Ta1, Ta18 and Ta13b) derived from subcloning of cosmid Qc 11H12 were sequenced. Candidate exons, strand and frame assignments were screened by the GRAIL program (Oak Ridge, RN). Oligonucleotide primers were designed according to the coding regions that presented highest homology score to 70K PMP in TA25, TA18, and TA13b. Ex13 and Ex3 are cDNA clones obtained by exon connection in 2-step-boosted or nested polymerase reactions (30 cycles with external primers and 40 cycles with internal primers) performed on oligo(dT)-primed cDNA Total RNA (20 μg) from a lymphoblastoid cell line was used as starting material. External primers correspond to positions 1,853–1, 872 (for Ex13), and to positions 1,854–1,874 and 2,357–2, 375 (for Ex3). Internal primers are indicated by arrows. Subsequent amplification products were blunt-ended by action of T4 DNA polymerase (New England Biolabs), directly cloned in pBlue-script KS⁺ vector (Stratagene), sequenced using dideoxynucleotide termination (applied Biosystems), and analysed on an automated DNA sequencer (Applied Biosystems).

FIGS. 4A–4B. Sequence alignment of ALD protein (SEQ ID NO:2) and human 70K PMP (SEQ ID NO:3). Amino acid identities are indicated by two dots and conservative changes by one. Sequence similarities were established with the FASTP program.

FIG. 6. Intron-exon boundaries of the ALD gene (SEQ ID NOS:4–17). First and last two bases of each exon are indicated in bold. The position (number between brackets) correspond to the published cDNA sequence (Mosser et al, Nature). The average size of the gap within the sequence is specified for large introns. Sequence of small introns is fully represented.

FIGS. 7A–7D. complete DNA sequence of the ALD gene (SEQ ID NOS:18–23). It contains both the cDNA sequence (in capital letters) and the intron sequence (in small letters).

DETAILED DESCRIPTION OF THE INVENTION

EXAMPLES

Figures 3A, 3B:
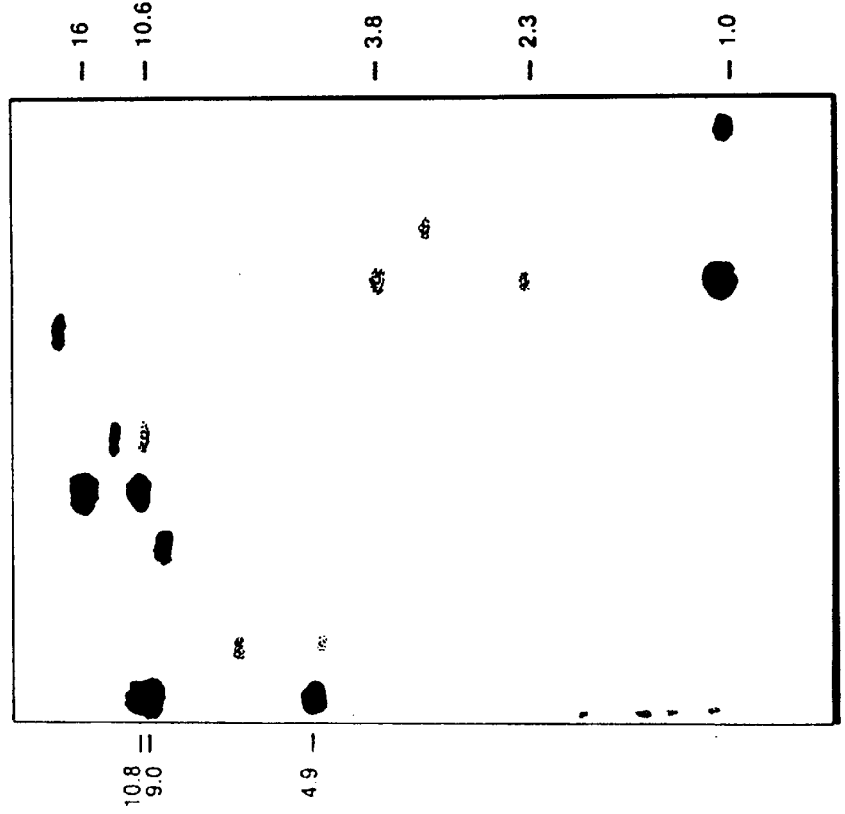
FIG. 3 a, Detection of deletions in the DNA isolated from three ALD patients using cDNA probe Ex13. DNA was digested with EcoRI (lates 1–4), HindTTT (lanes 5–8) and TaqI (lanes 9–12). Lanes 1, 5 and 9: normal woman; lanes 2, 6 and 10: patient L: lanes 3, 7 and 11: patient R; lanes 4, 8 and 12: patient Ma. The 10.8-kb EcoRI normal fragment (lanes 2–4) and the 12.5-kb HindIII abnormal junction fragment from patient R (lane 7) hybridize to only around 60 bp of the Ex13 probe and are thus very fait. Sizes (in kb) of normal restriction fragments are indicated on the left and on the right. Similar results were obtained with Ex3 in ALD patients deleted in 3' end region of the ALD gene. b, Northern blot analysis with probe ex13. cDNA Ex13 hybridized to northern blot (top) of human poly(A)⁺ RNA detects a transcript of 4.2 kb which is expressed in heart (H), placenta (P), lung (Lu), liver (Li) skeletal muscle (M), pancreas (Pa) and , to a lesser extent, in brain (B) and kidney (K). Two other transcripts are detected in heart and skeletal muscle (6.8 kb) and in liver and skeletal muscle (2.75 kb). RNA size markers are indicated on the left. A human β-actin probe hybridized to the same northern blot (bottom panel) detects two transcripts of 2.0 and 1.8 kb, respectively. METHODS. Gel electrophoresis, Southern blotting, probing and autoradiography were done as described. For b, human multiple-tissue northern blot was purchased from Clontech. Membranes were exposed at −70° C. to X-ray film for 5d (Ex13 or EX3 probes) or for 6 h (β-actin probe).
Figure 5:
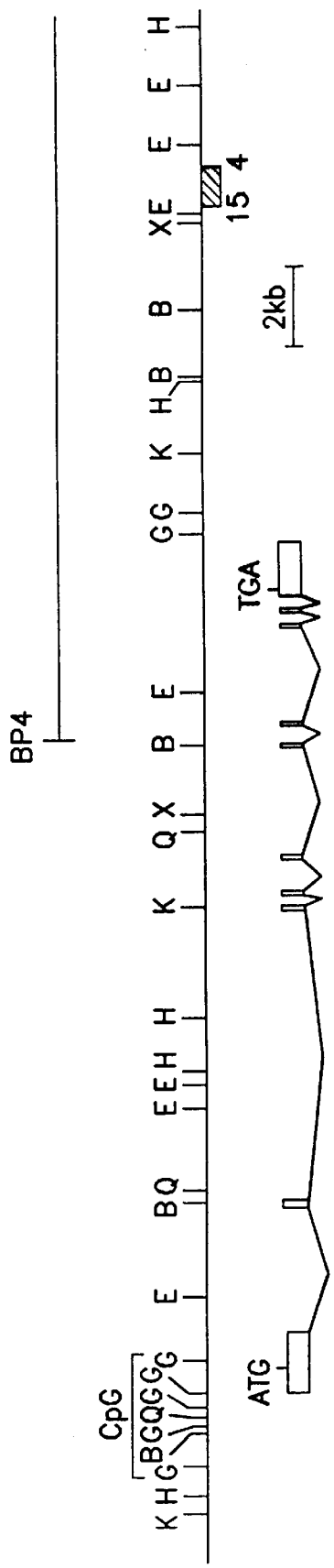
FIG. 5 Structural organization of the ALD gene The distribution of the 10 ALD exons is shown with black boxes. Traduction initiation and termination sites (respectively in exon 1 and 10) are indicated. The location of the CpG island, the genomic probe FR15.4 (grey box) and the most centromeric breakpoint of patient O rearrangement (BP4) are also represented.

I) Isolation and identification of the ALD gene

Here a positional cloning was used to identify a gene partially deleted in 6 of 85 independent patients with ALD. In familial cases, the deletions segregated with the disease. An identical deletion was detected in two brothers presenting with different clinical ALD phenotypes. Candidate exons were identified by computer analysis of genomic sequences and used to isolate complementary DNAs by exon connection and screening of cDNA libraries. The deduced protein sequence shows significant sequence identity to a peroxisomal membrane protein of $M_r$ 70K that is involved in peroxisome biogenesis and belongs to the "ATP-binding cassette" superfamily of transporters.

As previous attempts to purify VLCF-CoA synthetase were unsucessful, a "positional cloning" approach was used. The ALD locus has been mapped to Xq28 (deDuve, C. et al, Biochem. Pharmac. 23, 2495–2531, 1974), where the red/green colour pigment (R/GCP) genes reside. On the basis of the high incidence (40%) of colour vision anomalies in AMN patients and earlier results, it was firstly proposed that ALD and R/GCP genes could be close together. Recently, an AMN patient with blue-monochromatic colour vision was identified who had a complex rearrangement located 5' of the red-colour pigment (RCP) gene, which included two deletions separated by a large (>110 kb) inversion (FIG. 1a and b). Only the RCP gene was found in the first deletion (88 kb). No additional deletion was detected in this region in 81 other ALD patients. It was then postulated that the inverted segment or the second deletion were candidate loci for the ALD gene.

Probes corresponding to three of the breakpoints (B1') of this rearrangement were isolated (BP1, BP2 and BP3) (FIG. 1). To estimate the size of the second deletion, a probe 4 kb proximal to Fr15 was used (deleted in patient O; Martinex et al, Cell Biol. Int. Rep. 14,255–266 (1990) to obtain clones from a Xq28 cosmid library. Three overlapping clones were obtained that spanned about 90 kb and contained a cluster of rare restriction cutting sites (EagI, BssHII, SacII) indicating the presence of a CpG island (FIG. 1c). In parallel, an XbaI junction fragment (X-8) corresponding to breakpoints 4 and 2 in patient O was cloned (FIG. 1a). A restriction map of X-8 showed that a 1.8 kb XbaI-EcoRI (X2) fragment contains a 1.6-kb segment on the BP4 side and included within the Fr15 cosmid contig described above (FIG. 1c and c). Breakpoints 3 and 4 are separated by 19.2 kb, and delimit the second deletion in patient O.

To search for conserved sequences in other mammalian species and to detect additional deletions in other ALD patients, cosmid Qc 11H12 was subcloned (FIG. 1b, c). Probes TA25, TA1, TA18 and TA13B (FIG. 1c) showed cross-hybridization to various mammalian species. More important, X2, TA4, TA18 and Ta13a probes detected deletions in five other ALD patients. Probe X2 allowed the detection of a junction fragment segregating with the disease in family B (FIG. 1d). In another family (Ma), probe X2 detected an identical 22-kb HINDIII junction fragment in two brothers with different clinical phenotypes of ALD (FIG. 1e). The size of deletions ranged from 1.6 kb (patient B) to 15.3 kb (patient R) with partial overlap (FIG. 1c). Six patients had deletions (including patient O) in a population of 85 independent ALD patients, but no deletions were found in a panel of 82 control males. These results indicate that the region contains at least part of the ALD gene.

Figure 2A:
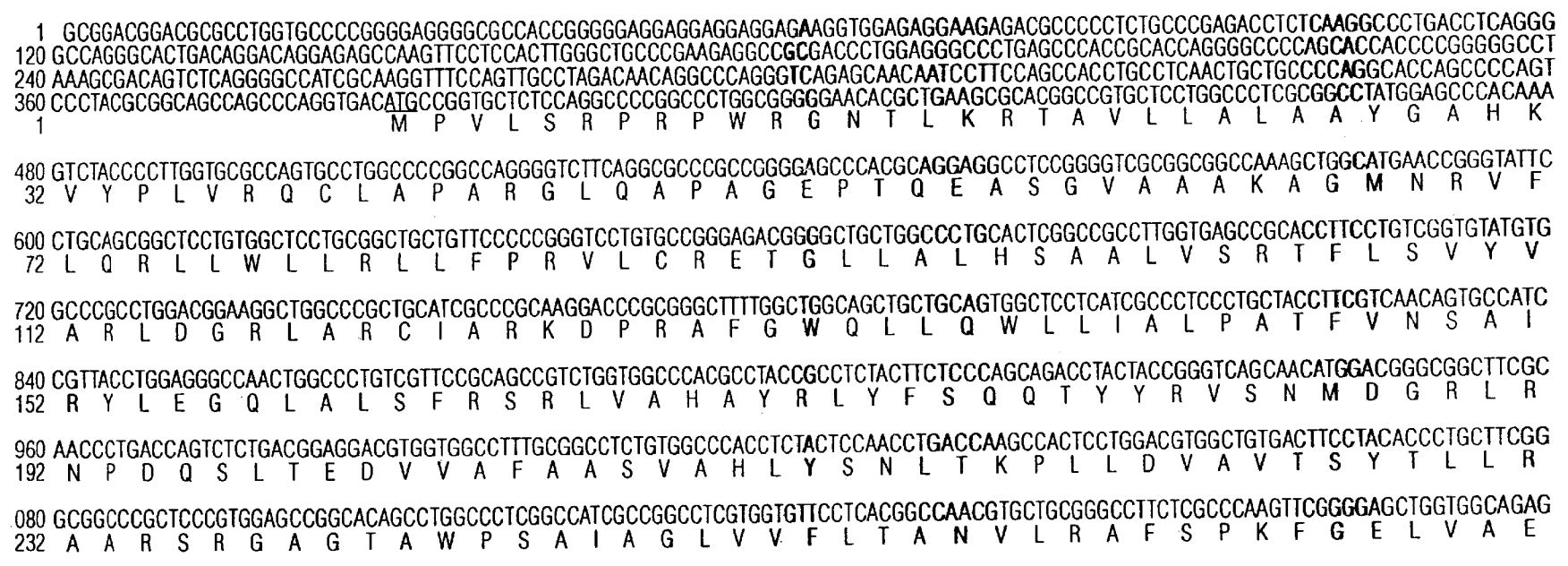

The sequences of probes Ta25, TA18, TA13b and of TA13a were determined and examined for putative coding regions (using a computer program based on a multiple sensor-neural network approach) revealed a large (>700 bp) putative protein coding sequence within TA25 and smaller open reading frames (300–400 bp) in TA18, TA13a and TA13b. The deduced amino-acid sequences showed significant sequence identity with collinearly positioned regions of human or rat 70K peroxisomal; membrane protein (PMP). Nested-PCR reactions using primers from the putative exons (FIG. 2) produced two fragments (EX13 and EX3) of sizes (645 bp and 498 bp, respectively) compatible with those expected from homology with the 70K PMP cDNA. They hybridized to the predicted DNA fragments in normal individuals and to the same fragments detected by genomic probes in ALD patients (FIG. 3a). Ex13 and Ex3 have been used in combination to screen a random-primed HeLa cell cDNA library to obtain 6 independent overlapping clones.

Figure 2B:
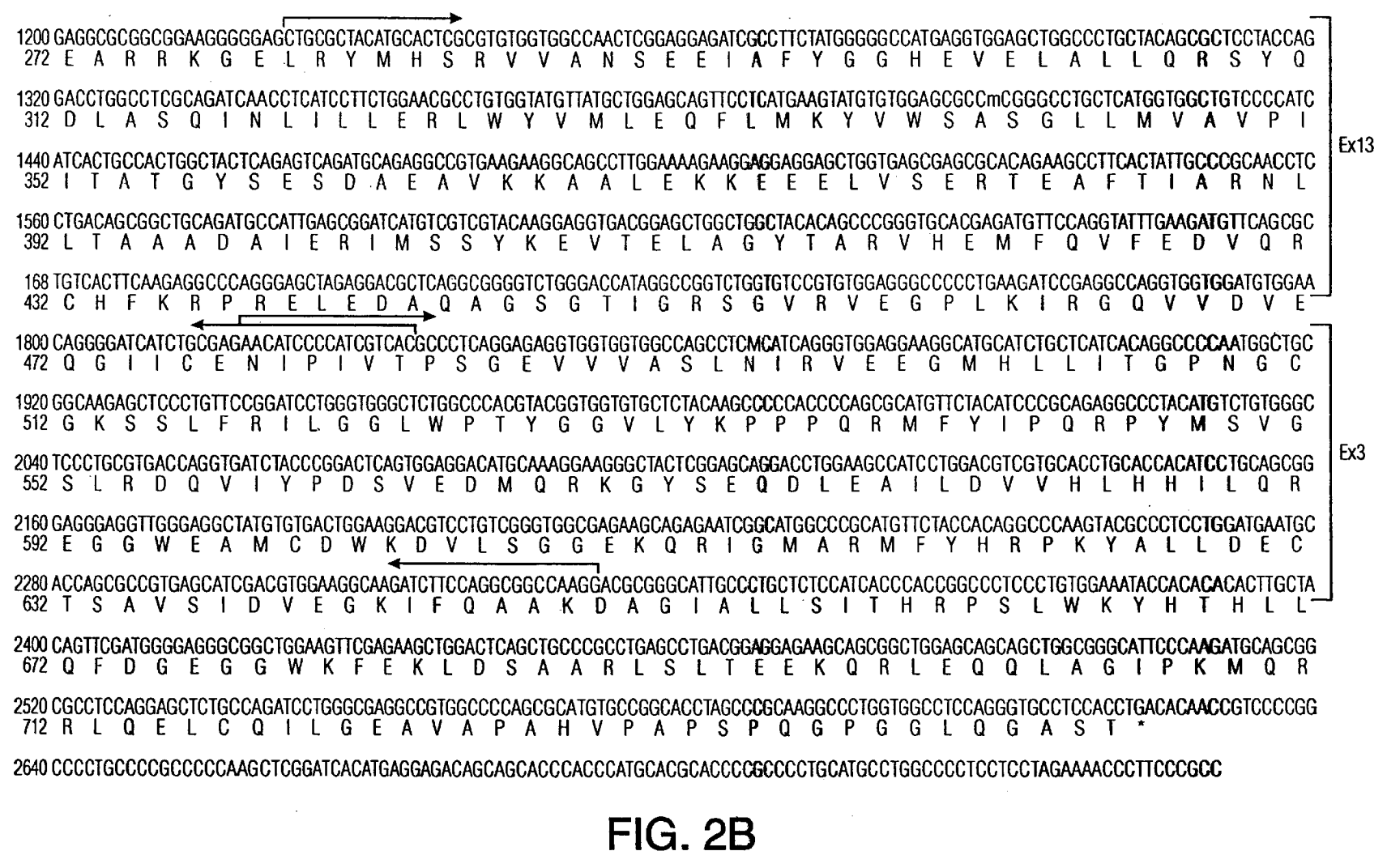

The 2,751-bp sequence (FIG. 2 (SEQ ID NO:1) contains the whole protein-coding sequence of 745 amino acids (SEQ ID NO:2). The first methionine codon is preceded by an in-phase stop codon (at bp 282) and is included within a potential ribosome-binding sequence. Significant sequence identity with the 70K PMP (SEQ IDNO:3) begins at methionine 67 and ends at around 680 (corresponding to the carboxy terminus of 70K PMP). The remaining 52 amino acid residues are unique to the ALD protein (FIG. 4B).

The sequence of ALD protein (SEQ ID NO:2) could be aligned with human 70K PMP (SEQ ID NO:3) (Saari, J. C. & Bredberg, L. Biochim. biophys. Acta 716, 226–272, 1982)) with only a few deletions or insertions, and revealed a 38.5% amino-acid identity (253/659 amino acids) (FIG. 4a). When conservative amino acids substitutions are considered, the sequence similarity between the two protein sequences reached 78.9%. The two proteins show a similar hydrophobicity profiles, with a hydrophobic amino-terminal region containing potential transmembrane segments.

The hydrophilic carboxy-terminal region of the ALD protein shows 56% identity over 210 amino acids to the corresponding region of 70K PMP. The two characteristic nucleotide-binding consensus sequences are almost identical between the two proteins (underlined in FIG. 4b).

When northern blots of poly (A)+ RNAs from human tissues were hybridized to probes Ex13 or Ex3, a transcript of 4,2 kb was detected in heart, placenta, lung, liver, skeletal muscle, testis, pancreas and, to a lesser extent, in brain and kidney (FIG. 3b). The expression of the 4.2-kb transcript was very low in adult brain but more marked in 21-week fetal brain. A second transcript of 6.8 kb was detected in heart and skeletal muscle, whereas a third transcript of 2.75 kb was detected in muscle and liver. These additional transcripts could arise from alternative processing or the use of multiple polyadenylation sites. The sequence shown in FIG. 2 corresponds to 4.2-kb messenger RNA, this being the only species detected in HeLa cells.

The putative ALD gene has thus been identified in the distal part of Xq28 which has deletions in one or several exons i 6 of 85 independent ALD patients. Some of these deletions are small and non-overlapping, thus strengthening the conclusion that this gene is indeed involved in ALD. Although the gene coding for VLCFA-CoA synthetase was considered as a candidate gene for ALD, a recently cloned rat gene for long-chain ($C_{12}$–$C_{16}$) acyl-CoA synthelase failed to detect homologous sequences on the X chromosome. The putative ALD gene shows no homology to this latter sequence, or to the three other enzymes involved in peroxisomal β-oxidation. Surprisingly, a very significant sequence identity was found with human and rat 70K PMP. Two putative domains could be identified by hydropathy analysis: an amino-terminal hydrophobic region, which presumably contains six transmembrane segments, and a hydrophilic region containing ATP-binding motifs with striking identity to the ATP-binding region of the human 70K PMP. This sequence is well conserved in the ATP-binding cassette (ABC) family of transporters, which includes the multidrug-resistant gene product, the cystic fibrosis transmembrane conductance regulator, and the products of the PSF1 and PSF2 genes, which encode peptide transporters and map in the class II region of the human MHC complex (FIG. 4b). The conserved region includes the A and B consensus sequences (A; G-X4-G-K-T-X6-I/V; B: R/K-X3-G-X3-L (hydrophobic)4-D) of a nucleotide-binding fold, plus a 12-amino-acid motif highly conserved in ABC proteins (FIG. 4b).

ALD protein must therefore be a member of this super-family of ABC transporters, which are also involved in transport of proteins, amino acids, inorganic ions and peptides in prokaryotes and eukaryotes. Although the predicted sequence of ALD protein (SEQ ID NO:2) shows significant identity to 70K PMP (SEQ ID NO:3), no homology was found to 35K PMP or to other PMPs required for peroxisome biogenesis in yeast. Although ALD was initially thought to involve a deficiency in peroxisomal VLCFA-CoA synthesase, the predicted sequence of the putative ALD protein rather suggests a protein involved in transport of VLCFA-CoA synthetase into the peroxisomal membrane or a protein that is functionally associated with the VLCFA-CoA synthetase in the peroxisomal membrane. The translocation of acyl-CoA oxidase, the next enzyme or the peroxisomal β-oxidation pathway, requires ATP hydrolysis, whereas the transport of VLCFA across the peroxisomal membrane does not, and neither is it impaired in peroxisomes from ALD patients.

Expression of ALD protein was observed in every tissue tested, but the relationship between ALD protein expression and the abundance of peroxisomes in tissues may not be straight-forward. Perosisomes are particularly abundant in liver and kidney, having an average diameter of 0.2–1 $\mu$M. In other tissues, including the brain and fibroblasts, they are less abundant and smaller (0.05–0.2 $\mu$M). This abundance and size difference may reflect a distinct membrane and matrix protein compositions of peroxisomes in different tissues. Although ALD is associated with a defective oxidation of VLCFA, this metabolic defect is mainly expressed in brain and adrenal tissues.

ALD is characterized by a striking variation in clinical phenotype. In family Ma, an identical deletion was found in two sibs, a boy who developed cerebral ALD at 8 years, and his brother who developed only very mild adrenal insufficiency at 13 years. Furthermore, deletions were associated with the adult form (patient O and R) as well as with the severe childhood form (patients B and L). These differences suggest that the phenotypic variability of ALD is probably due to secondary factors (possibly immunological) or to the influence of still unidentified modifier genes.

II) Transfer and expression of the cDNA sequence of the ALD gene 1) retroviral vector A defective murine Moloney vector (Mo-MLV) is used.

The defective vector still contains its cis-sequences such as the LTR sequence or part thereof sufficient for the transcription and integration, the psi sequence necessary for the encapsidation and the PB sequence for viral replication. In this vector the viral genes gag, pol, env are at least partly deleted.

The promoter of the ALD gene or advantageously a stronger promoter such as the PGK-1 promoter (phosphoglycerate kinase) or SV10 promotor replaces the deleted viral gene.

The cDNA of the ALD gene is cloned within the defective vector, under the control of the promoter, in a chosen restriction site.

The retroviral vector is then introduced in a cell line for encapsidation, which cell line expressed the gag, pol and env viral genes. A cell line like NIH/3T3 previously modified with the helper virus (Danos et al, PNAS, 85, 6460–6465, 1988) is used.

The recombinant construct is introduced by transfection and the cells produce viral particles.

2) Infection of cells

The cells used for the transfer of the cDNA sequence are cultivated and contacted and incubated with the retroviral vector. The infected cells are then amplified sufficiently to be used for the treatment.

We claim:

1. An isolated protein comprising the amino acid sequence of SEQ ID NO:2.

2. An isolated protein comprising the amino acids residues 694 to 745 of SEQ ID NO:2.

3. An isolated polypeptide comprising at least 7 contiguous amino acid residues from residues 694–745 of SEQ ID NO:2, wherein said polypeptide is recognized by antibodies that bind specifically the amino acid sequence from residues 694–745 of SEQ ID NO:2.

* * * * *